US010610310B2

(12) United States Patent
Todd et al.

(10) Patent No.: US 10,610,310 B2
(45) Date of Patent: Apr. 7, 2020

(54) USER INTERFACE SYSTEM AND METHODS FOR OVERLAYING SURGICAL VIDEO OUTPUT

(71) Applicants: Robin Elizabeth McKenzie Todd, Toronto (CA); David Bruce McFadzean, Toronto (CA); Monroe Milas Thomas, Toronto (CA); Sam Anthony Leitch, Toronto (CA)

(72) Inventors: Robin Elizabeth McKenzie Todd, Toronto (CA); David Bruce McFadzean, Toronto (CA); Monroe Milas Thomas, Toronto (CA); Sam Anthony Leitch, Toronto (CA)

( * ) Notice: Subject to any disclaimer, the term of this patent is extended or adjusted under 35 U.S.C. 154(b) by 252 days.

(21) Appl. No.: 15/722,481

(22) Filed: Oct. 2, 2017

(65) Prior Publication Data

US 2019/0099225 A1   Apr. 4, 2019

(51) Int. Cl.
*A61B 34/00* (2016.01)
*A61B 17/3205* (2006.01)
(Continued)

(52) U.S. Cl.
CPC .......... *A61B 34/25* (2016.02); *A61B 17/3205* (2013.01); *A61B 90/37* (2016.02); *G06F 3/048* (2013.01); *G06T 11/00* (2013.01); *H04N 5/23296* (2013.01); *H04N 5/44504* (2013.01); *A61B 34/76* (2016.02); *A61B 90/30* (2016.02); *A61B 90/361* (2016.02); *A61B 2017/00119* (2013.01); *A61B 2017/00199* (2013.01); *A61B 2017/00203* (2013.01); *A61B 2017/00973* (2013.01); *A61B 2034/105* (2016.02); *A61B 2034/207* (2016.02); *A61B 2034/2055* (2016.02); *A61B 2034/2065* (2016.02); *A61B 2034/256* (2016.02); *A61B 2090/064* (2016.02);
(Continued)

(58) Field of Classification Search
CPC .................... A61B 34/25; A61B 2090/365
See application file for complete search history.

(56) References Cited

U.S. PATENT DOCUMENTS 10,231,781 B2 *   3/2019   Waisman .............. A61B 18/22
2001/0034530 A1 * 10/2001  Malackowski ........ A61B 90/36
                                                606/130
(Continued)

*Primary Examiner* — David N Werner
(74) *Attorney, Agent, or Firm* — Perry + Currier Inc.

(57) ABSTRACT

A surgical user interface system and methods, involving: an interface having at least one overlay element of: at least one menu bar, at least one tab, at least one sidebar, at least one window, at least one icon; at least one graphical control element, at least one haptic control element, and at least one voice control element, the interface configured to: communicate with at least one surgical system, the at least one surgical system having at least one of an imaging system, a guidance system, a control system, a tracking system, a navigation system, a drive system, and a voice recognition system; display information corresponding to at least one surgical parameter of the at least one surgical system; overlay a real-time streaming image from the imaging system; receive input by way of the at least one overlay element; transmit the input to the at least one surgical system; and update, in real-time, the at least one overlay element in response to a change in the at least one surgical parameter.

27 Claims, 8 Drawing Sheets

(51) Int. Cl.
  *H04N 5/445*    (2011.01)
  *H04N 5/232*    (2006.01)
  *G06T 11/00*    (2006.01)
  *G06F 3/048*    (2013.01)
  *A61B 34/20*    (2016.01)
  *A61B 17/00*    (2006.01)
  *A61B 34/10*    (2016.01)
  *A61B 90/00*    (2016.01)
  *A61B 90/30*    (2016.01)
  *G06F 3/0481*   (2013.01)
  *G06F 3/0482*   (2013.01)
  *G06F 3/0484*   (2013.01)
  *G06K 9/20*     (2006.01)
  *G06K 9/32*     (2006.01)
  *G06T 7/20*     (2017.01)

(52) U.S. Cl.
  CPC ... *A61B 2090/066* (2016.02); *A61B 2090/364* (2016.02); *A61B 2090/365* (2016.02); *A61B 2090/372* (2016.02); *A61B 2217/005* (2013.01); *G06F 3/0482* (2013.01); *G06F 3/0484* (2013.01); *G06F 3/04817* (2013.01); *G06K 9/2054* (2013.01); *G06K 9/3208* (2013.01); *G06T 7/20* (2013.01); *G06T 2207/10016* (2013.01); *G06T 2207/30244* (2013.01); *H04N 5/23216* (2013.01)

(56) References Cited

U.S. PATENT DOCUMENTS

| | | | |
|---|---|---|---|
| 2007/0078678 A1* | 4/2007 | DiSilvestro | G06Q 50/22 705/2 |
| 2009/0036902 A1* | 2/2009 | DiMaio | A61B 34/10 606/130 |
| 2009/0131821 A1* | 5/2009 | Speeg | A61B 10/0275 600/566 |
| 2010/0225209 A1* | 9/2010 | Goldberg | A61B 34/30 312/209 |
| 2015/0100091 A1* | 4/2015 | Tohmeh | A61B 17/7083 606/279 |
| 2017/0265943 A1* | 9/2017 | Sela | G06F 19/00 |
| 2018/0168781 A1* | 6/2018 | Kopelman | A61C 1/0015 |
| 2018/0228343 A1* | 8/2018 | Seeber | A61B 34/35 |
| 2018/0256272 A1* | 9/2018 | Maeda | A61B 90/50 |

* cited by examiner

USER INTERFACE SYSTEM AND METHODS FOR OVERLAYING SURGICAL VIDEO OUTPUT

TECHNICAL FIELD

Generally, the present disclosure technically relates to user interface systems and methods. More particularly, the present disclosure technically relates to user interface systems and methods for surgical systems. Even more particularly, the present disclosure technically relates to user interface systems and methods for overlaying surgical video output from a surgical system.

BACKGROUND

In the related art, user interfaces for surgical systems tend to be limited in the features that are controllable by a surgeon. For example, image-guided neurosurgery typically relies on preoperative imaging information that is subject to errors resulting from brain shift and deformation in the operating room (OR). A related art graphical user interface (GUI) facilitates the flow of data from OR to image volume for providing the neurosurgeon with updated views concurrent with surgery. Upon acquisition of registration data for patient position in the OR (using fiducial markers), a Matlab® GUI displays ultrasound image overlays on patient-specific, preoperative magnetic resonance (MR) images. Registration matrices are applied to patient-specific anatomical models used for image updating. After displaying the re-oriented brain model in OR coordinates and digitizing the edge of the craniotomy, mapping of the brain is simulated using a finite element model (FEM). Based on the FEM, interpolation to the resolution of the preoperative images is performed and re-displayed to the surgeon during the procedure.

However, these related art systems have experienced many challenges, including an inaccessibility of information presented on a graphic user interface (GUI) by a surgeon during implementing guidance or drive procedures while imaging, wherein the surgeon cannot independently operate a drive or guidance system, and wherein a clinical applications specialist is necessitated. Therefore, a need exists for a user interface system and methods that facilitates independent operation of a drive or guidance system by a surgeon.

SUMMARY

In addressing at least many of the challenges experienced in the related art, a user interface system and methods are described by the present disclosure which facilitate independent operation of a drive or guidance system by a surgeon and which eliminate the necessity for a clinical applications specialist.

In accordance with an embodiment of the present disclosure, a surgical user interface system, comprises: an interface comprising at least one overlay element of: at least one menu bar, at least one tab, at least one sidebar, at least one window, at least one icon; at least one graphical control element, at least one haptic control element, and at least one voice control element, the interface configured to: communicate with at least one surgical system, the at least one surgical system comprising at least one of an imaging system, a guidance system, a control system, a tracking system, a navigation system, a drive system, and a voice recognition system; display information corresponding to at least one surgical parameter of the at least one surgical system; overlay a real-time streaming image from the imaging system; receive input by way of the at least one overlay element; transmit the input to the at least one surgical system; and update, in real-time, the at least one overlay element in response to a change in the at least one surgical parameter.

In accordance with an embodiment of the present disclosure, a method of providing a surgical user interface system, comprising: providing an interface comprising providing at least one overlay element of: at least one menu bar, at least one tab, at least one sidebar, at least one window, at least one icon; at least one graphical control element, at least one haptic control element, and at least one voice control element, providing the interface comprising configuring the interface to: communicate with at least one surgical system, the at least one surgical system comprising at least one of an imaging system, a guidance system, a control system, a tracking system, a navigation system, a drive system, and a voice recognition system; display information corresponding to at least one surgical parameter of the at least one surgical system; overlay a real-time streaming image from the imaging system; receive input by way of the at least one overlay element; transmit the input to the at least one surgical system; and update, in real-time, the at least one overlay element in response to a change in the at least one surgical parameter.

In accordance with an embodiment of the present disclosure, a method of interfacing at least one surgical system by way of a surgical user interface system, comprising: providing the surgical interface system, providing the surgical interface system comprising providing an interface comprising at least one overlay element of: at least one menu bar, at least one tab, at least one sidebar, at least one window, at least one icon; at least one graphical control element, at least one haptic control element, and at least one voice control element, the interface configured to: communicate with at least one surgical system, the at least one surgical system comprising at least one of an imaging system, a guidance system, a control system, a tracking system, a navigation system, a drive system, and a voice recognition system; display information corresponding to at least one surgical parameter of the at least one surgical system; overlay a real-time streaming image from the imaging system; receive input by way of the at least one overlay element; transmit the input to the at least one surgical system; and update, in real-time, the at least one overlay element in response to a change in the at least one surgical parameter; and overlaying the surgical interface system in relation to the real-time streaming image from the imaging system.

Some of the features in the present disclosure are broadly outlined in order that the section, entitled Detailed Description, is better understood and that the present contribution to the art by the present disclosure is better appreciated. Additional features of the present disclosure are described hereinafter. In this respect, understood is that the present disclosure is not limited in its implementation to the details of the components or steps as set forth herein or as illustrated in the several figures of the Drawing, but are capable of being carried out in various ways which are also encompassed by the present disclosure. Also, understood is that the phraseology and terminology employed herein are for illustrative purposes in the description and are not regarded as limiting.

BRIEF DESCRIPTION OF THE DRAWING

The above, and other, aspects, and features, of the several embodiments in the present disclosure will be more apparent from the following Detailed Description as presented in conjunction with the following several figures of the Drawing.

Figure 1:
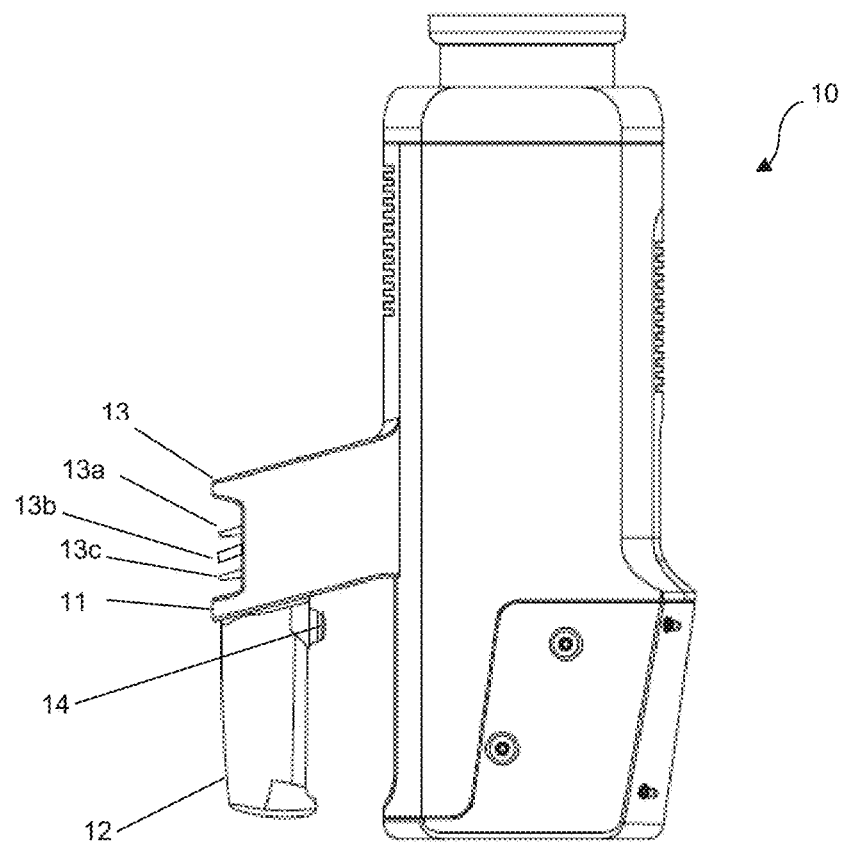
FIG. 1 is a diagram illustrating a perspective view of an end effector having a plurality of end effector control features, operable with a surgical user interface system, as shown in FIG. 12, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, well-understood elements that are useful or necessary in commercially feasible embodiment are often not depicted to facilitate a less obstructed view of these various embodiments of the present disclosure.

DETAILED DESCRIPTION

A surgical user interface system S (FIG. 12), a method M1 of providing the system S (FIG. 13), and a method M2 of interfacing at least one surgical system by way of the system S (FIG. 14), described herein, are useful in surgical technologies, such as imaging, guidance, and tracking, e.g., as used in relation to neurosurgery, including oncological care, neurodegenerative disease, stroke, brain trauma, and orthopedic surgery. The subject matter of the present disclosure is applicable to imaging, guidance, and tracking in relation to other conditions or fields of medicine. Noted is that, while the present disclosure describes examples in the context of imaging, guidance, and tracking in relation to neurosurgery, the subject matter of the present disclosure is applicable to other surgical procedures that may use imaging, such as MRI. The system S and the methods M1 and M2 may be implemented with the Synaptive® Modus V™ user interface as well as the Synaptive® Drive™ user interface.

Various example apparatuses or processes are below-described. No below-described example embodiment limits any claimed embodiment; and any claimed embodiments may cover processes, products of manufacture, compositions of matter, devices, systems, or apparatuses that differ from those examples described below. The claimed embodiments are not limited to apparatuses or processes having all the features of any one of the processes, products of manufacture, compositions of matter, devices, systems, or apparatuses below-described or to features common to multiple or all the processes, products of manufacture, compositions of matter, devices, systems, or apparatuses below-described. The claimed embodiments optionally comprise any of the below described processes, products of manufacture, compositions of matter, devices, systems, or apparatuses.

Furthermore, numerous specific details are set forth in order to provide a thorough understanding of the disclosure. However, understood is that the embodiments described herein are practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof denote the specified features, steps, or components that are included. These terms are not to be interpreted to exclude the presence of other features, steps or components.

As used herein, the term "exemplary" or "example" denotes "serving as an example, instance, or illustration," and should not be construed as preferred or advantageous over other configurations disclosed herein.

As used herein, the terms "about," "approximately," and "substantially" are intended to cover variations that may exist in the upper and lower limits of the ranges of values, such as variations in properties, parameters, and dimensions. In one non-limiting example, the terms "about," "approximately," and "substantially" are understood to denote plus or minus 20 percent or less than a described value.

Unless defined otherwise, all technical and scientific terms used herein are intended to have the same meaning as understood by one of ordinary skill in the art. Unless otherwise indicated, such as through context, as used herein, the following technical and scientific terms are intended to have the meanings as understood by one of ordinary skill in the art.

Figure 12:
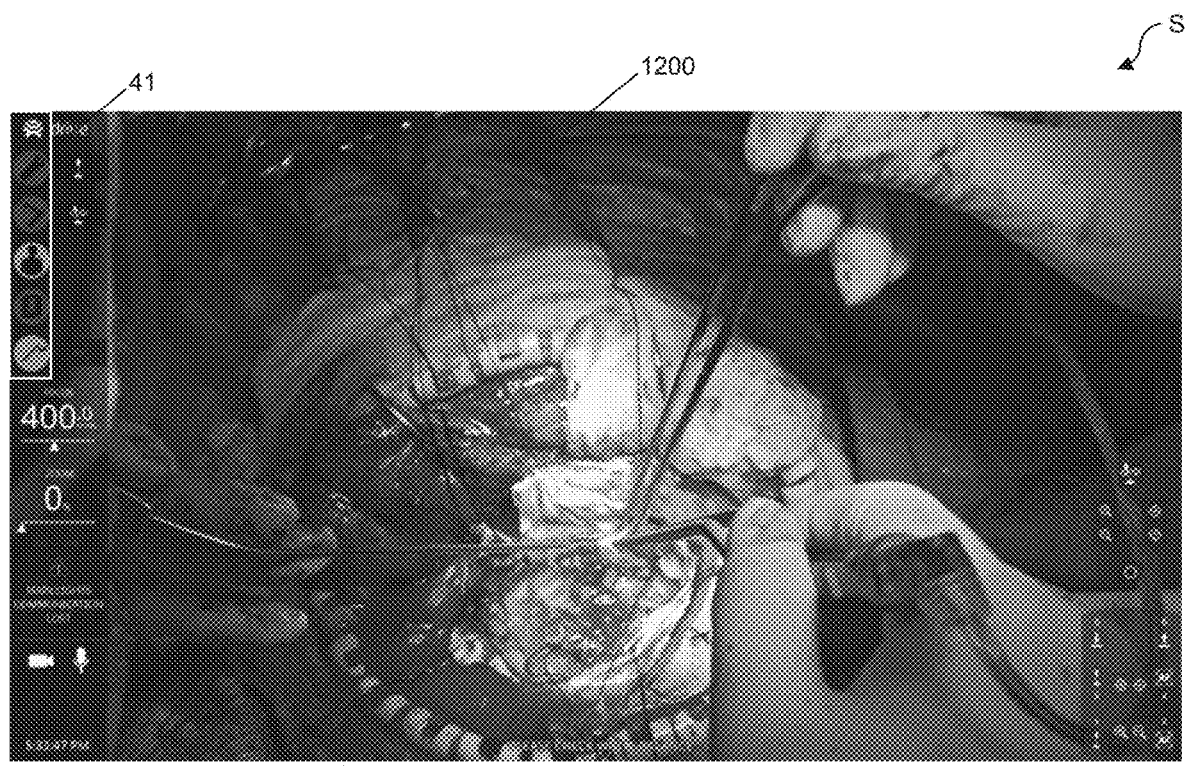
FIG. 12 is a screenshot illustrating a surgical overlay screen of a Synaptive® Drive™ user interface, operable with a surgical interface system, for facilitating at least one surgical procedure, in accordance with an embodiment of the present disclosure.

Referring to FIG. 1, this diagram illustrates, in a perspective view, an end effector 10 having a plurality of end effector control features 11, operable with a surgical user interface system S, as shown in FIG. 12, in accordance with an embodiment of the present disclosure. The end effector 10 is disposed at a distal end of an arm, e.g., a robotic arm (not shown) of a drive system (not shown). The plurality of control features 11 comprises at least one of: a handle 12, at least one switch 13, and at least one trigger 14. The end effector 10 is operable by manually actuating at least one of the handle 12, the at least one switch 13, and the at least one trigger 14 to respectively effect: adjusting zoom and focus, toggling between manual positioning modes, and manually positioning the arm.

Still referring to FIG. 1, the at least one switch 13 comprises a zoom adjustment switch 13a configured to operate by: manually pressing the zoom adjustment switch 13a in an upward direction to zoom-in by approximately 20% and by manually pressing the zoom adjustment switch 13a in a downward direction to zoom-out by approximately 20%, wherein the zoom adjustment switch 13a does not have a continuous function, e.g., pressing and holding the zoom adjustment switch 13a does not continuously adjust a zoom level; manually releasing the zoom adjustment switch 13a and manually re-pressing the zoom adjustment switch 13a in an upward direction to further zoom-in by approximately another 20% and by manually pressing the zoom adjustment switch 13a in a downward direction to further zoom-out by approximately another 20%. The at least one switch 13 further comprises a focus adjustment switch 13b configured to operate by: manually pressing the focus adjustment switch 13b in an upward direction to increase a focal distance and by manually pressing the focus adjustment switch 13b in a downward direction to decrease the focal distance.

Still referring to FIG. 1, the at least one switch 13 further comprises a positioning mode toggle switch 13c configured to operate by at least one "joystick" mode of: manually rolling the positioning mode toggle switch 13c to rotate the end effector 10, wherein the end effector 10 has an orientation that is fixed in space, whereby an image, e.g., as shown in FIG. 12, displayed on a display device (now shown), e.g., a monitor, from a camera feed is reoriented; manually axially depressing the positioning mode toggle switch 13c to move the end effector 10 toward or away from a target, e.g., a portion of the cerebral tissue as shown in FIG. 12, to which the camera (not shown) is aimed, wherein the end effector 10 retains its orientation relative to the camera's current orientation; manually translating the positioning mode toggle switch 13c to move the end effector 10 in at least one of an x-direction, a y-direction, and a z-direction, wherein the end effector 10 retains its orientation in relation to the camera's current orientation, whereby a different point of the target in a surgical field is viewable; manually orbiting the positioning mode toggle switch 13c to move the end effector 10 around the target at a constant distance, wherein the end effector 10 continues aiming at the target, whereby the target is viewable from a plurality of orientations; and manually actuating the positioning mode toggle switch 13c in a free motion, wherein the positioning mode toggle switch 13c moves freely in all directions, but is not assisted by a force moment sensor, to move only one joint of the arm at a time, e.g., to reposition the arm if a mechanical limit is reached. The at least one trigger 14 comprises a manual positioning mode trigger configured to operate by depressing the manual positioning mode trigger to manually position the arm by using a selected positioning mode.

Figure 2:
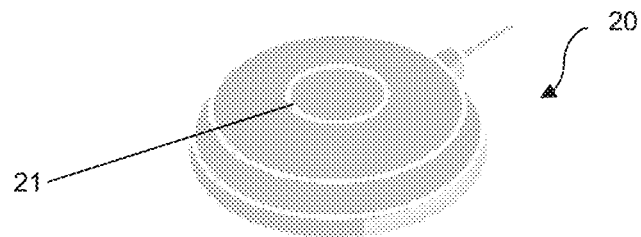
FIG. 2 is a diagram illustrating a perspective view of a "simple" or single function foot pedal, operable with a surgical user interface system, as shown in FIG. 12, in accordance with an embodiment of the present disclosure.
Figure 3:
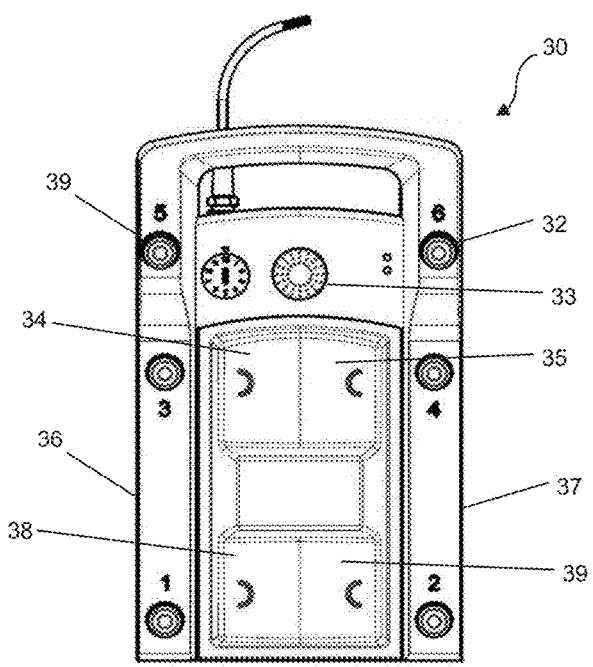
FIG. 3 is a diagram illustrating a perspective view of a multifunction foot pedal, operable with a surgical user interface system, as shown in FIG. 12, in accordance with an embodiment of the present disclosure.

Referring to FIG. 2, this diagram illustrates, in a perspective view, a "simple" or single function foot pedal 20, operable with a surgical user interface system S, as shown in FIG. 12, in accordance with an embodiment of the present disclosure. The surgical user interface system S is operable with the Synaptive® Modus V™ user interface, the Synaptive® Modus V™ user interface configured to operate with at least one foot pedal configuration of: the "simple" or single function foot pedal 20 configured to control only an arm movement relating to an arm alignment; and a multi-function pedal 30 configured to control an arm movement relating to an arm alignment as well as a plurality of video functions (FIG. 3). The single function foot pedal 20 is operable by way of a foot actuated toggle switch 21 to effect an incremental movement.

Referring to FIG. 3, this diagram illustrates, in a perspective view, a multifunction foot pedal 30, operable with a surgical user interface system S, as shown in FIG. 12, in accordance with an embodiment of the present disclosure. The multifunction foot pedal 30 comprises at least one of: an "in" positioning arm stand-off control feature 31; an "out" positioning arm stand-off control feature 32; an optional designable control feature 33; a video focus-in control feature 34; a video focus-out control feature 35; a positioning arm auto-align control feature 36; a video auto-focus toggling feature 37; a video zoom-in feature 38; and a video zoom-out feature 39.

Figure 4:
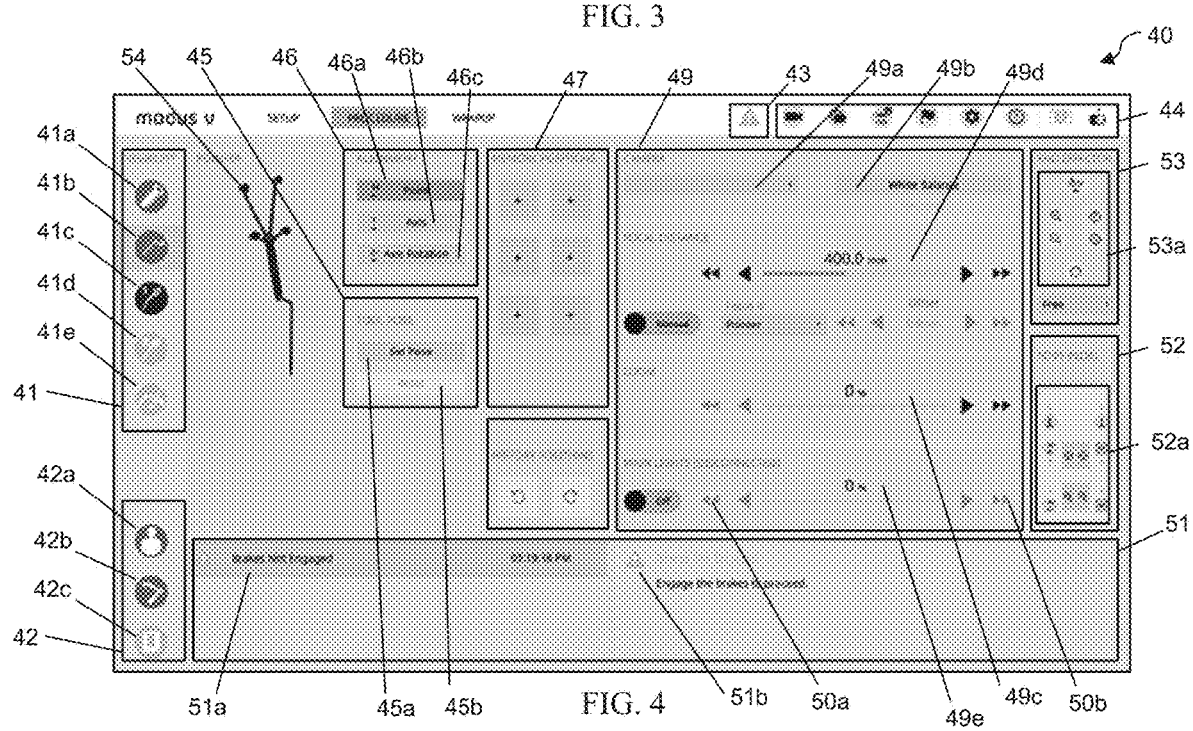
FIG. 4 is a screenshot illustrating a procedure screen of a Synaptive® Modus V™ user interface, operable with a surgical user interface system, as shown in FIG. 12, for facilitating at least one surgical procedure, in accordance with an embodiment of the present disclosure.

Referring to FIG. 4, this screenshot illustrates a procedure screen 40 of a Synaptive® Modus V™ user interface, operable with a surgical user interface system S, as shown in FIG. 12, for facilitating at least one surgical procedure, in accordance with an embodiment of the present disclosure. The procedure screen 40 is implemented for a procedure phase in the Synaptive® Modus V™ tracking system's workflow during a surgical procedure. In the procedure phase, a user may: select an instrument to track, whereby a tracked instrument is selectable; indicate a manner in which the Synaptive® Modus V™ tracking system (not shown) aligns an optical device, e.g., a camera, to the tracked instrument; save selections and move to memorized positions; move backward and forward through a history of the arm's positions; and adjust zoom, focus, and light parameters. The Synaptive® Modus V™ tracking system comprises a positioning arm on a mobile base, peripheral devices, such as tracking cameras and monitors, and trackable surgical instruments or tools.

Still referring to FIG. 4, the procedure screen 40 displays at least one of: a tool tracking sidebar, e.g., a tool sidebar 41, comprising a plurality of tool icons 41a, 41b, 41c, 41d, 41e, wherein tapping each tool icon of the plurality of tool icons 41a, 41b, 41c, 41d, 41e effects tracking a corresponding tool (not shown); a reference tracking sidebar, e.g., a reference sidebar 42, comprising a plurality of reference icons 42a, 42b, 42c, wherein tapping a reference icon of the plurality of reference icons 42a, 42b, 42c effects indicating a tracking status of at least one of a patient reference (not shown), an end effector 10, and a calibration block (not shown); a notification icon 43, wherein the notification icon 43 appears if a notification available for viewing; a plurality of status and task icons 44; a pose setup window 45; and an optical device alignment options window 46 comprising a plurality of option buttons, such as a point button 46a, an axis adjustment button 46b, and an axis rotation button 46c, wherein tapping an option button effects indicating a manner in which the optical device should align with the tracked tool.

Still referring to FIG. 4, the procedure screen 40 further displays a memory position window 47 comprising at least one of: a plurality of memory position buttons 47a, 47b, 47c, 47d, 47e, each memory position button or icon having a "plus" sign representation for saving position information, wherein tapping each memory position button 47a, 47b, 47c, 47d, 47e effects recording a new memory position, whereby each memory position button 47a, 47b, 47c, 47d, 47e indicates a position index number, and wherein tapping each memory position button 47a, 47b, 47c, 47d, 47e, having the position index number, and actuating the foot pedal 30 effect moving the end effector 10 into a corresponding saved position, and wherein further tapping each memory position button 47a, 47b, 47c, 47d, 47e, having the position index number, effects editing corresponding information to reset or delete a previously saved memory position; and an edit button 47g. The procedure screen 40 further displays a position history window 48 comprising an undo button 48a and a redo button 48b, wherein tapping the undo button 48a and actuating the foot pedal 30 effects moving the arm, e.g., a positioning arm into a previous position, wherein tapping the redo button 48b and actuating the foot pedal 30 effects moving the arm back into an original position.

Still referring to FIG. 4, the procedure screen 40 further displays at least one of: a camera and lights control window 49 comprising a camera and light control feature 50 having increment adjustment icons. By default, the fine increment arrows 50a, 50b adjust the slider value by approximately 1%; and the coarse increment arrows adjust the slider value by approximately 10%, wherein these values are changeable via an increments settings screen of the Synaptive® Modus V™ user interface; a notification dialog box 51 for displaying warnings or notifications relating to a surgical task being performed; a foot pedal status window 52 having a plurality of foot pedal function icons 52a for indicating control status of each foot pedal function of the multi-function foot pedal 30 (FIG. 3), wherein each foot pedal function icon 52a of the plurality of foot pedal function icons 52a comprises a blue color when its corresponding control is operating; and an end effector status window 53 comprising a plurality of end effector function icons 53a for indicating status of a plurality of end effector controls (FIG. 1), such as status of the zoom and focus controls on the end effector handle 12 and the currently-selected manual mode, wherein each end effector function icon 53a comprises a blue color when its corresponding control is operating.

Figure 5:
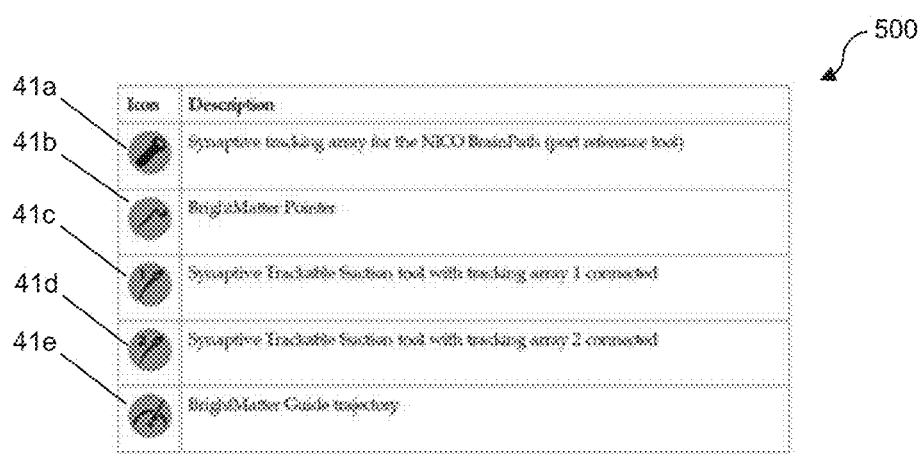
FIG. 5 is a table cross-referencing a plurality of tool icons in a tool tracking sidebar of the procedure screen, as shown in FIG. 4, in accordance with an embodiment of the present disclosure.

Referring to FIG. 5, this table 500 cross-references the plurality of tool icons 41a through 41e in a tool sidebar 41 of the procedure screen 40, as shown in FIG. 4, in accordance with an embodiment of the present disclosure. The tool sidebar 41 comprises the plurality of tool icons 41, e.g., respectively, a tracking array icon 41a, corresponding to a tracking array, such as a Synaptive® tracking array for a NICO® BrainPath® (port reference tool); a pointer tool icon 41b, corresponding to a pointer tool, such as Synaptive® BrightMatter™ pointer tool; a suction tool icon 41c, corresponding to a suction tool having a first tracking array, such as a Synaptive® trackable suction tool with a first tracking array; a suction tool icon 41d, corresponding to a suction tool having a second tracking array, such as a Synaptive® trackable suction tool with a second tracking array; and a guide trajectory icon 41e, corresponding to a guide trajectory, such as a BrightMatter™ Guide™ trajectory.

Figure 6:
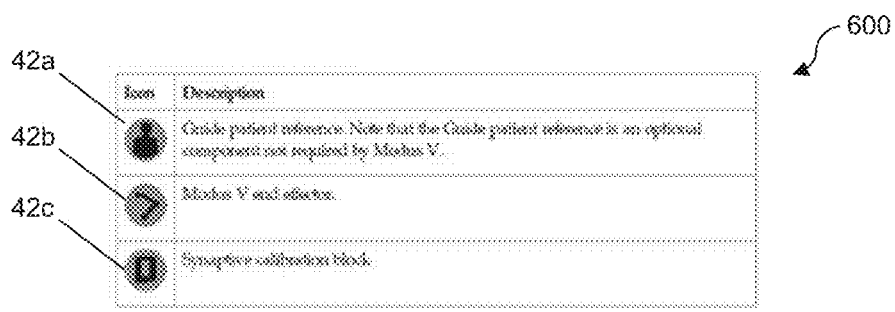
FIG. 6 is a table cross-referencing a plurality of reference icons in a reference tracking sidebar of the procedure screen, as shown in FIG. 4, in accordance with an embodiment of the present disclosure.

Referring to FIG. 6, this table 600 cross-references the plurality of reference icons 42a through 42c of a reference sidebar 42 of the procedure screen 40, as shown in FIG. 4, in accordance with an embodiment of the present disclosure. The reference sidebar 42 comprises the plurality of reference icons 42a, 42b, 42c, e.g., respectively, an optional guide patient reference icon 42a, corresponding to a patient reference, such as Guide™ patient reference; an end effector reference icon 42b, corresponding to a reference for the end effector 10, such as relating to an end effector; and a calibration block reference icon 42c, corresponding to a calibration block reference, such as relating to a Synaptive® calibration block.

Figure 7:
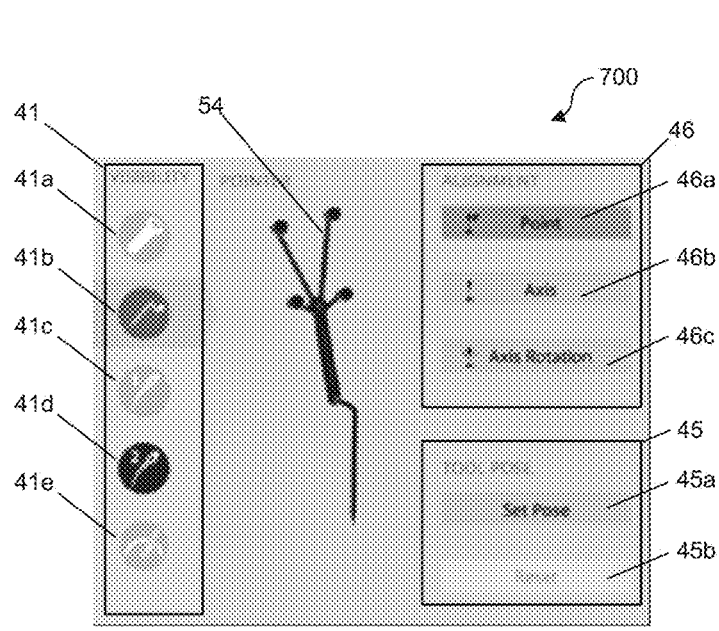
FIG. 7 is a partial screenshot illustrating the plurality of tool icons, a pointer tool representation, the pose setup window, and the optical device alignment options window of the procedure screen, as shown in FIG. 4, in accordance with an embodiment of the present disclosure.

Referring to FIG. 7, this partial screenshot illustrates, in a screen portion 700 of the procedure screen 40, as shown in FIG. 4, the tool sidebar 41, comprising the plurality of tool icons 41; a pointer tool alignment representation 54; a pose setup window 45; and an optical device alignment options window 46, in accordance with an embodiment of the present disclosure. A variety of tool alignment features are displayed on the procedure screen 40. The tool alignment features are used to position the end effector 10 at a consistent or a constant distance, consistent or a constant angle, and consistent or a constant rotation relative to a tool (not shown). The tracking system (not shown) is configured to track the location of the tool (not shown) as the user works and moves the end effector 10 into a "pose" for the tool when an alignment move is initiated. The pointer tool alignment representation 54 is updateable in real-time in response to any change made via at least one of the pose setup window 45 and optical device alignment options window 46.

Still referring to FIG. 7, in setting a tool pose, the position of an end effector relative to a tool, e.g., a tracked tool, is referred to as a "pose." A pose is defined by the following parameters: (a) a distance of the end effector from the tracked tool; (b) an angle of the end effector relative to the tracked tool; and (c) a rotation of the end effector relative to the tracked tool. In particular, the tracking system is configured with a default pose for the Synaptive® BrightMatter™ pointer tool and the Synaptive® tracking array for the NICO® BrainPath® (also called the "port reference" tool). For trackable suction tools having a plurality of different configurations, such tools do not have an associated default pose. By using the tool pose setup icons, comprising a set pose button 45a and a pose reset button 45b, in the pose setup window 45, the pose for the currently selected tool may be set. To set the pose, the user manually positions the end effector 10 at a desired distance, a desired rotation, and a desired angle in relation to the tool and taps the set pose button 45a.

Still referring to FIG. 7, when setting a pose, the end effector 10 should be disposed at a distance from the tool, wherein the end effector 10 does not collide with the tool, and wherein the end effector 10 provides adequate magnification and focus for the camera. For a trackable suction tool, its pose is set when holding the trackable suction tool in a comfortable position, wherein the tool tip is centered as displayed on a display device, such as a monitor, e.g., a primary surgeon monitor. A currently-selected camera alignment option, e.g., from the optical device alignment options window 46, comprising a plurality of option buttons, such as a point button 46a, an axis adjustment button 46b, and an axis rotation button 46c, does not affect setting a pose. The tracking system records the angle, rotation, and distance of the end effector 10 from the tracked tool when setting a pose. To restore the default pose for a Synaptive®BrightMatter™ pointer tool or a port reference tool, the user taps the pose reset button 45b.

Figure 8:
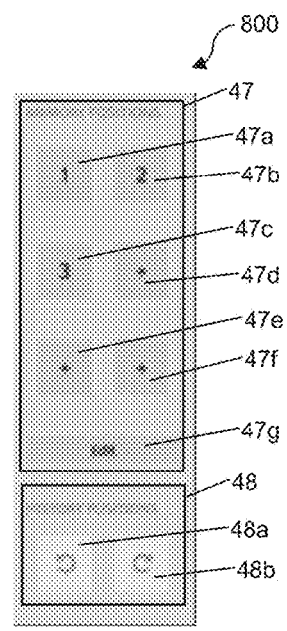
FIG. 8 is a partial screenshot illustrating a position memory window and a position history window of the procedure screen, as shown in FIG. 4, in accordance with an embodiment of the present disclosure.

Referring to FIG. 8, this partial screenshot illustrates a position memory window 47 and a position history window 48 in a screen portion 800 of the procedure screen 40, as shown in FIG. 4, in accordance with an embodiment of the present disclosure. The memory position window 47 comprises a plurality of memory position buttons 47a, 47b, 47c, 47d, 47e, each memory position button or icon having a "plus" sign representation for saving position information, wherein tapping each memory position button 47a, 47b, 47c, 47d, 47e effects recording a new memory position, whereby each memory position button 47a, 47b, 47c, 47d, 47e indicates a position index number, and wherein tapping each memory position button 47a, 47b, 47c, 47d, 47e, having the position index number and actuating the foot pedal 30 effects moving the end effector 10 into a corresponding saved position. The position memory window 47 further comprises an edit button 47g, and wherein further tapping the edit button 47g and tapping each memory position button 47a, 47b, 47c, 47d, 47e, having the position index number, effects editing corresponding information to reset or delete a previously saved memory position Still referring to FIG. 8, in the screen portion 800, the procedure screen 40 further displays a position history window 48 comprising an undo button 48a and a redo button 48b, wherein tapping the undo button 48a and actuating the foot pedal 30 effects moving the arm, e.g., a positioning arm having the end effector 10, into a previous position, wherein tapping the redo button 48b and actuating the foot pedal 30 effects moving the arm, having the end effector 10, back into an original position. When moving the arm, having the end effector 10, into a memory position via the position history window 48 or a history position via the position history window 48, the tracking system does not enforce a minimum standoff distance to prevent a collision with a patient, s surgeon, or a surgical tool. The user may carefully observe the positioning arm, having the end effector 10, when moving into these positions and stop the motion if necessary. The positioning arm may not always follow the same route when moving into memory positions or when moving backward and forward through history positions. The user may observe the positioning arm carefully when it is moving into these positions and stop motion if necessary. However, the user interface system S (FIG. 12) facilitates collision avoidance by providing enhanced control of the surgical systems.

Still referring to FIG. 8, in the screen portion 800, the memory position features, e.g., a position memory window 47 and a position history window 48, are used to move the end effector 10 into a recorded position, regardless of the current location of the tracked tool. Memory positions are positions for which the user can set, and to which the end effector 10 can return, on demand. History positions are the previous positions in which the end effector 10 has been disposed. When the user taps a memory position icon, e.g., a memory position button 47a, 47b, 47c, 47d, 47e, or a history position icon, e.g., an undo button 48a and a redo button 48b, the Synaptive® Modus V™ tracking system ignores the tracked tool, whereby features for setting a pose and for selecting an alignment type are rendered unavailable.

For switching to aligning a tool, the user may tap a tool icon of the plurality of tool icons 41a, 41b, 41c, 41d, 41e in the tool sidebar 41.

Still referring to FIG. 8, in the screen portion 800, by example only, in working with memory positions via the position memory window 47, the Modus V™ tracking system's memory positions feature, e.g., the plurality of memory position buttons 47a, 47b, 47c, 47d, 47e is used to save up to six memory positions and move to the end effector 10 among these saved positions during the surgical procedure. To save a memory position, the following steps are performed: (a) moving the positioning arm, having the end effector 10, into a desired pose (either by manually moving the arm or by completing an alignment movement), (b) setting a desired zoom and a desired focus distance, e.g., (c) tapping a "+" icon to record that memory position, whereby a confirmation message is displayed; and repeating steps (a), (b), and (c), whereby up to six memory positions are savable. The undo button 48a and redo button 48b are configured to respectively effect movement of the arm with the end effector 10 backwards and forwards through a stack of history positions. If an undo movement or a redo movement is not available, the undo button 48a or the redo button 48b is displayed with a dark gray background color. The method M2 (FIG. 14) comprises any of the operational steps herein described.

Still referring to FIG. 8, in the screen portion 800, by example only, to move into the last arm position, the user may tap the undo button 48a. The undo button 48a then becomes a blue color to indicate that the history position has been selected. The user may press and hold the foot pedal 30 to move the positioning arm with the end effector 10 into the previous position. The drive or guidance system moves the positioning arm with the end effector 10 into the previous position in the memory stack, corresponding to previous positions or "history" positions, and stops the movement when the positioning arm with the end effector 10 reaches the previous position or the foot pedal 30 is released. The user can press and hold the foot pedal 30 again to move the positioning arm with the end effector 10 to the next previous history position in the memory stack. To undo this movement, the user may tap the redo button 48b and then press and hold the foot pedal 30 to move the positioning arm with the end effector 10. The drive or guidance system moves the positioning arm with the end effector 10 back into the original position. The positioning arm with the end effector 10 stops movement when it reaches the original position or the redo button 48b is released.

Still referring to FIG. 8, in the screen portion 800, by example only, the memory stack of history positions is erased when the drive or guidance system's mobile base brakes are disengaged, wherein the user may restart the surgical procedure or the user may reboot the drive or guidance system. The functionalities of the undo button 48a and the redo button 48b become unavailable when the user restarts or reboots; and the undo button 48a and the redo button 48b become a dark gray color. The drive or guidance system cannot undo movements that result in a collision of the positioning arm. The manual mode switch is used to manually move the positioning arm out of a collision course. Movements that result in the positioning arm reaching its mechanical limit are not added to the memory stack of history positions. If the positioning arm reaches a mechanical limit, the user may tap the undo button 48a then press and hold the foot pedal 30 to return the positioning arm with the end effector 10 to the previous position.

Figure 9:
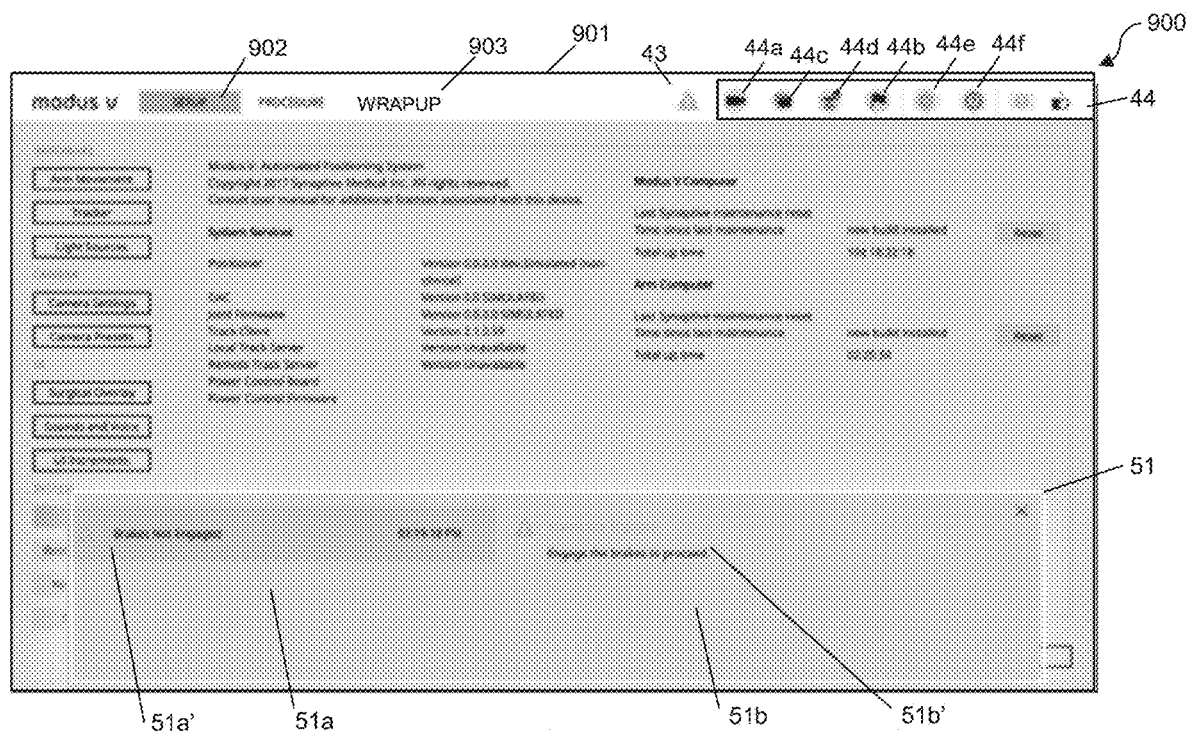
FIG. 9 is a screenshot illustrating a "setup" or settings screen of a Synaptive® Modus V™ user interface for facilitating at least one surgical procedure, operable with a surgical user interface system, as shown in FIG. 12, in accordance with an embodiment of the present disclosure.

Referring to FIG. 9, this screenshot illustrates a "setup" or settings screen 900 of a user interface, e.g., a Synaptive® Modus V™ user interface, for facilitating at least one surgical procedure, in accordance with an embodiment of the present disclosure. The Synaptive® Modus V™ user interface uses three types of notifications to inform the user relating to the current state of the drive or guidance system: (1) spoken notifications; (2) text notifications via a notification dialog box 51; and (3) sounds. With respect to spoken notifications, the Synaptive® Modus V™ user interface provides spoken notifications that confirm the user input or inform the user about actions being performed. For example, when the user selects a memory position "1," Synaptive®Modus V™ user interface speaks the text "Position one selected." In most cases, these notifications are self-explanatory. In some cases, the Synaptive® Modus V™ user interface provides a spoken notification to inform the user of an issue relating to the drive or guidance system.

Still referring to FIG. 9, in the screen 900, the Synaptive® Modus V™ user interface may also display a text message in a software user interface with information about such issue, e.g., via the notification region 51a, and any action the user can take to resolve such issue, e.g., via the notification region 51b. When the user is working in the "setup" or settings screen 900, text notifications appear at the bottom of the "setup" or settings screen 900, e.g., in the notification dialog box 51. A notification icon 43 also appears beside a taskbar, e.g., the plurality of status and task icons 44, at the top of the screen 900. If the user is working in the "Setup" screen via the setup tab 902, the "Wrap-up" screen via the wrap-up tab 903, or "Settings" screen via the settings tab (not shown), by way of a dashboard 901, the user can tap the notification icon 43 to bring up the notification in a notification dialog box 51. The user may tap the "close" icon ("X") to dismiss the notification dialog box 51. The Synaptive® Modus V™ user interface uses sounds to acknowledge the user inputs and to inform the user about certain drive and guidance system states.

Still referring to FIG. 9, in the screen 900, notifications are displayed until they are resolved in one of three ways: (1) timing-out, wherein some notifications disappear automatically after a few seconds, and wherein timing-out is implemented for simple informational notifications; (2) changing the underlying condition causing the notification, e.g., for example, the "Brakes not engaged" notification, e.g., via the notification region 51a, disappears when the user engage the brakes; and (3) acknowledging the notification, e.g., by the user, wherein some notifications require the user to acknowledge the information in them by tapping an "Acknowledge" or acknowledgement button (not shown) on the screen 900, e.g., when the Synaptive® Modus V™ user interface displays a notification indicating that the user are increasing the light intensity beyond a safe threshold, the user must tap the "Acknowledge" button (not shown) in the notification before the user can continue using the Synaptive® Modus V™ user interface.

Figure 10:
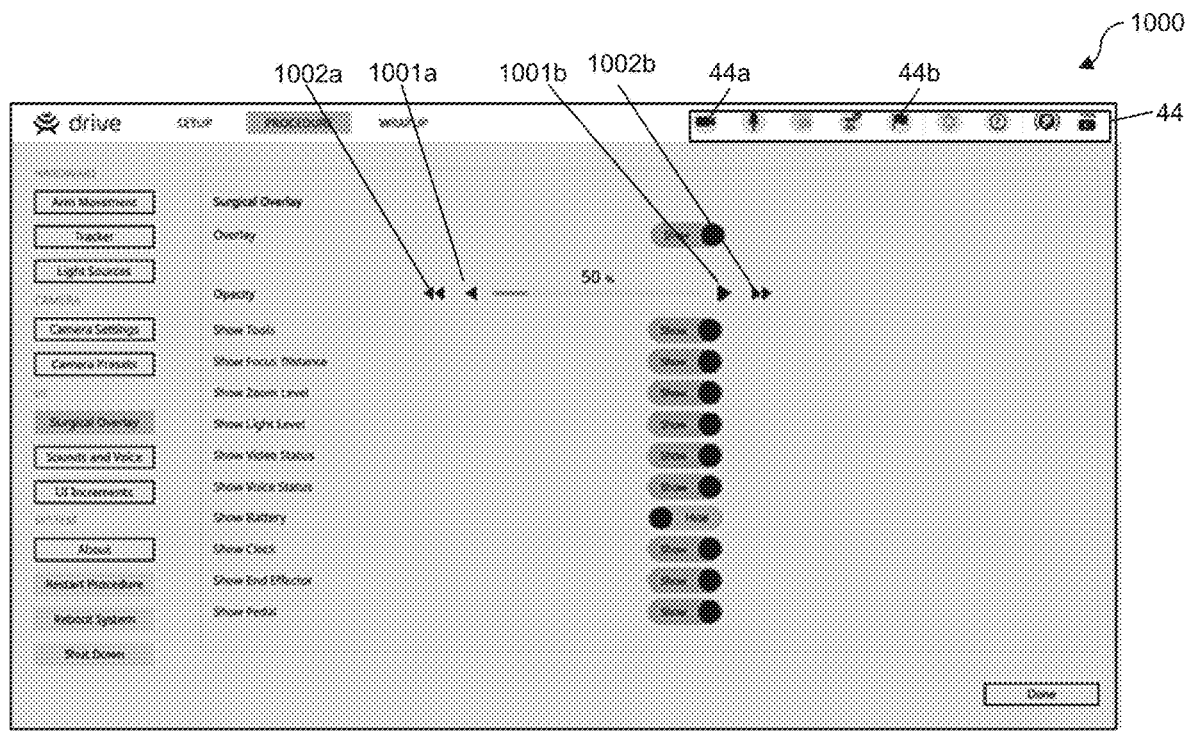
FIG. 10 is a screenshot illustrating a surgical overlay settings screen of a Synaptive® Drive™ user interface for facilitating at least one surgical procedure, operable with a surgical user interface system, as shown in FIG. 12, in accordance with an embodiment of the present disclosure.

Referring to FIG. 10, this screenshot illustrates a surgical overlay settings screen 1000 of a Synaptive® Drive™ user interface, operable with the surgical user interface system S (FIG. 12), for facilitating at least one surgical procedure, in accordance with an embodiment of the present disclosure. The Synaptive® Drive™ user interface renders the surgical overlay settings screen 1000 which is implemented to control the appearance of the information overlaying in image rendered on a display, e.g., via a primary surgeon's monitor, wherein the image comprises a real-time streaming video feed (FIG. 12). For instance, a parameter, comprising opacity, is respectively adjustable by depressing and holding buttons 1001a, 1001b, 1002a, 1002b.

Figure 11:
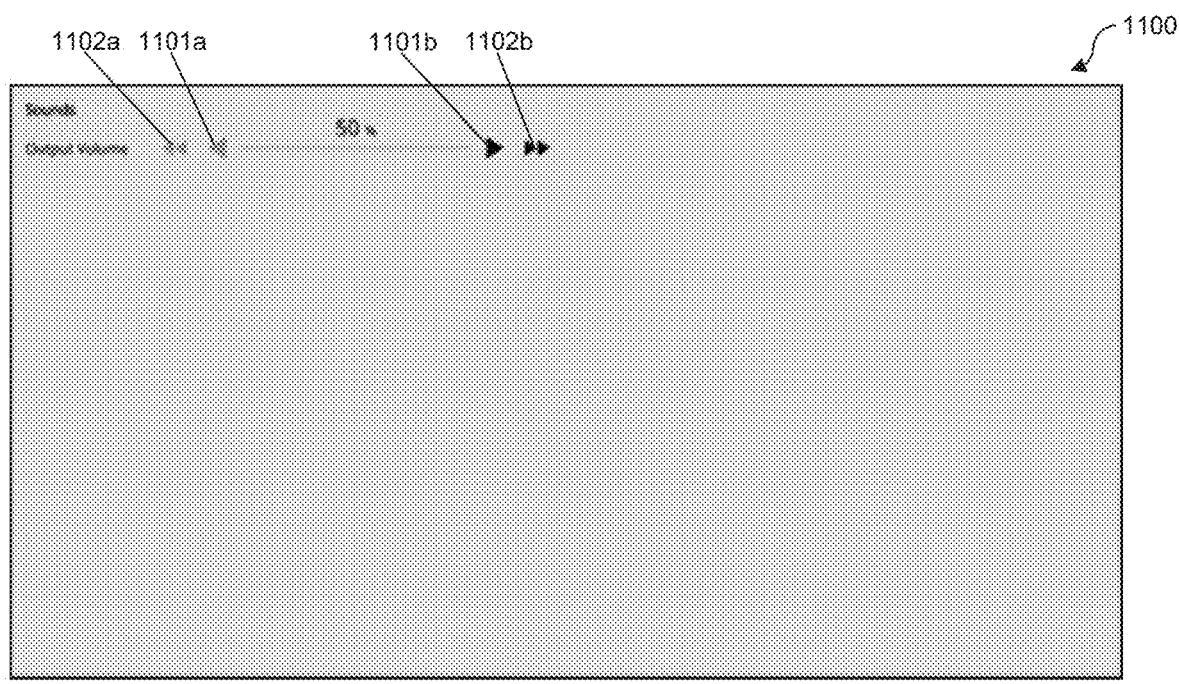
FIG. 11 is a screenshot illustrating a sound settings screen of a Synaptive® Drive™ user interface for facilitating at least one surgical procedure, operable with a surgical user interface system, as shown in FIG. 12, in accordance with an embodiment of the present disclosure.

Referring to FIG. 11, this screenshot illustrating a sound settings screen 1100 of a Synaptive® Drive™ user interface, operable with the surgical user interface system S (FIG. 12), for facilitating at least one surgical procedure, in accordance with an embodiment of the present disclosure. The Synaptive® Drive™ user interface renders the sound settings screen 1100 which is implemented to control the sound level or sound output volume. The user may use the sound settings screen 1100 by tapping and holding the arrow icons 1101a, 1101b to respectively decrease or increase the sound volume within a predetermined sound level range. The user may use the sound settings screen 1100 by tapping and holding the arrow icons 1102a, 1102b to respectively decrease or increase the sound volume at a minimum sound level or a maximum sound level.

Referring to FIG. 12, this screenshot illustrating a surgical overlay screen 1200 of a surgical interface system S for facilitating at least one surgical procedure, in accordance with an embodiment of the present disclosure. The surgical overlay screen 1200 provides information that overlays an image being rendered on a display (not shown), e.g., a primary surgeon's monitor, wherein the image comprises a real-time streaming video feed 200, by example only. In general, the surgical user interface system S, comprises: an interface, such as an overlay screen, e.g., the screen 40 (FIG. 4), the screen 90 (FIG. 9), the surgical overlay screen 1200, and the like, comprising at least one overlay element of: at least one menu bar, at least one tab, at least one sidebar, at least one window, at least one icon; at least one graphical control element, at least one haptic control element (not shown), and at least one voice control element, the interface configured to: communicate with at least one surgical system (not shown), the at least one surgical system comprising at least one of an imaging system, a guidance system, a control system, a tracking system, a navigation system, a drive system, and a voice recognition system (not shown); display information corresponding to at least one surgical parameter of the at least one surgical system; overlay a real-time streaming image 200 from the imaging system (not shown); receive input by way of the at least one overlay element; transmit the input to the at least one surgical system; and update, in real-time, the at least one overlay element in response to a change in the at least one surgical parameter.

Still referring to FIG. 12 and referring back to FIGS. 4 and 9, in the system S, the at least one sidebar comprises at least one of: a tool tracking sidebar, e.g., a tool sidebar 41, configured to communicate with the tracking system, the tool tracking sidebar comprising at least one tool tracking icon, such as the plurality of tool icons 41a, 41b, 41c, 41d, 41e, each tool tracking icon of the at least one tool tracking icon corresponding to at least one surgical tool; and a reference tracking sidebar (not shown in FIG. 12, but this option is shown in FIG. 4), e.g., the reference sidebar 42, configured to communicate with the tracking system, the reference tracking sidebar comprising at least one reference tracking icon, such as the plurality of reference icons 42a, 42b, 42c, each reference icon of the at least one reference tracking icon corresponding to at least one reference object, e.g., respectively, an optional guide patient reference icon 42a, corresponding to a patient reference, such as a Synaptive® Guide™ patient reference; an end effector reference icon 42b, corresponding to a reference for the end effector 10, such as relating to an end effector 10; and a calibration block reference icon 42c, corresponding to a calibration block reference, such as relating to a Synaptive® calibration block (not shown). The at least one surgical tool (not shown) comprises at least one of a tracked pointer tool, a tracked calibration tool, and a tracked suction tool, a tracked resection tool; and the at least one reference object (not shown) comprises at least one of a patient reference object, and end effector 10, and a calibration apparatus.

Still referring to FIG. 12 and referring back to FIGS. 4 and 9, in the system S, each tool tracking icon such as the plurality of tool icons 41a, 41b, 41c, 41d, 41e, comprises a color, the color being real-time updateable in response to at least one of tracking and navigating registration of each corresponding at least one surgical tool. The color comprises one of: a red color, a yellow color, and a green color, wherein the red color indicates that the corresponding at least one surgical tool is not registered, wherein the yellow color indicates that the corresponding at least one surgical tool is within a predetermined threshold of being registered, and wherein the green color indicates that the corresponding at least one surgical tool is registered.

Still referring to FIG. 12 and referring back to FIGS. 4 and 9, in the system S, the at least one menu bar comprises at least one of: a notification icon 43, the notification icon 43 configured to render if at least one notification is received from the guidance system; and a status and task menu bar 44, the status and task bar 44 comprising at least one of a video recording icon 44a, a mark log icon 44b, a video overlay icon 44c, a tracking camera icon 44d, a settings icon 44e, a help icon 44f, and a caster brake icon (not shown). The notification icon 43 comprises a representation of an exclamation mark disposed within a triangle.

Still referring to FIG. 12 and referring back to FIGS. 4 and 9, the notification icon 43 comprises a color, the color being real-time updateable in response to a change in the drive or guidance system, wherein the color comprises one of a red color and a yellow color, wherein the red color indicates an error arising corresponding to a change in the at least one surgical system which will result in patient injury, and wherein the yellow color indicates a warning corresponding to a change in the at least one surgical system which may result in patient injury.

Still referring to FIG. 12 and referring back to FIGS. 4 and 9, in the system S, the video recording icon 44a is configured to toggle for respectively commencing and terminating video recording. The mark log icon 44b is configured to toggle for adding a flag to a log of the guidance system. The video overlay icon 44c is configured to toggle for respectively displaying or hiding the at least one overlay element. The tracking camera icon 44d is configured to toggle for indicating a status of the guidance system in relation to the tracking system. The settings icon 44e is configured to toggle for accessing at least one of at least one setting and at least one option of the guidance system. The help icon 44f is configured to toggle for accessing help information. The caster brake icon (not shown) is configured to toggle for indicating a status of a caster brake.

Still referring to FIG. 12 and referring back to FIGS. 4 and 9, in the system S, the at least one window comprises at least one of a pose setup window 45, an optical device alignment options window 46, a position memory window 47, a position history window 48, a camera and light control window 49, a notification dialog box 51, a foot pedal status window, and an end effector status window. The pose setup window 45 comprises a set pose button 45a and a reset button 45b, wherein the set pose button 45a is configured to set a position of the at least one surgical tool in relation to an end effector 10 as a current position, whereby the position defines a pose set, and wherein the reset button 45b is configured to set the position of the at least one surgical tool in relation to the end effector 10 as a default position.

Still referring to FIG. 12 and referring back to FIGS. 4 and 9, in the system S, the an optical device alignment options window 46 comprises at least one of comprising a plurality of alignment option buttons, such as a point button 46a, an axis adjustment button 46b, and an axis rotation button 46c, wherein the point button 46a is configured to initiate an instruction to the guidance system for moving an arm, with an end effector 10, to position a camera of the tracking system, whereby the camera is oriented toward a desired portion of the at least one surgical tool, wherein the axis rotation button 46c is configured to initiate an instruction to the guidance system for moving the arm, with an end effector 10, to position the camera of the tracking system, whereby the camera is oriented toward a desired portion of the at least one surgical tool, and whereby the camera is aligned with the at least one surgical tool at an angle relative to a major axis of the at least one surgical tool, the angle specified by the pose set, and wherein the axis rotation button 46c is configured to initiate an instruction to the guidance system for moving the arm, with an end effector 10, to position the camera of the tracking system, whereby the camera is oriented toward a desired portion of the at least one surgical tool, whereby the camera is aligned with the at least one surgical tool at an angle relative to a major axis of the at least one surgical tool, the angle specified by the pose set, and whereby the camera is aligned with the at least one surgical tool at a rotation, the rotation specified by the pose set.

Still referring to FIG. 12 and referring back to FIGS. 4 and 9, in the system S, the position memory window 47 comprises a plurality of memory position buttons 47a, 47b, 47c, 47d, 47e, each memory position button or icon having a "plus" sign representation for saving position information and configured to toggle for recording a new memory position, wherein the at least one memory position button becomes at least one numbered memory position button, wherein the at least one numbered memory position button is configured to receive input corresponding to at least one actuation of a foot pedal of the guidance system, wherein the at least one numbered memory position button is configured to initiate at least one of resetting a memory position and deleting a memory position.

Still referring to FIG. 12 and referring back to FIGS. 4 and 9, in the system S, the position history window 48 comprises an undo button 48a and a redo button 48b, wherein the undo button 48a is configured to initiate an instruction to the guidance system for moving the arm with the end effector 10 into a previous position in response to an actuation of a foot pedal 30, and wherein the redo button 48b is configured to initiate an instruction to the guidance system for moving the arm with the end effector 10 into an original position in response to an actuation of a foot pedal 30.

Still referring to FIG. 12 and referring back to FIGS. 4 and 9, in the system S, the camera and lights controls window 49 comprises a camera and light control feature 50 having increment adjustment icons, the camera and light control feature 50 comprises at least one of: a camera preset adjustment feature comprising at least one of a field selection feature 49a and a white balance control feature 49b, a magnification adjustment feature 49c, a focal distance adjustment feature 49d, and an incremental light adjustment feature 49d. The notification dialog box 51 comprises at least one notification region, e.g., notification regions 51a, 51b for respectively displaying at least one of a warning 51a' and a notification 51b' relating to a surgical task being performed.

Still referring to FIG. 12 and referring back to FIGS. 4 and 9, in the system S, the foot pedal status window 52 comprises at least one foot pedal function icon 52a corresponding to at least one function of a multi-function foot pedal 30 of a drive or guidance system, wherein the at least one foot pedal function icon 52a comprises a color, wherein the color comprises one of a gray color and a blue color, wherein the gray color indicates that a corresponding function is not being performed by the multi-function foot pedal 30, and wherein the blue color indicates that a corresponding function is being performed by the multi-function foot pedal 30. The multifunction foot pedal 30 comprises at least one of: an "in" positioning arm stand-off control feature 31; an "out" positioning arm stand-off control feature 32; an optional designable control feature 33; a video focus-in control feature 34; a video focus-out control feature 35; a positioning arm auto-align control feature 36; a video auto-focus toggling feature 37; a video zoom-in feature 38; and a video zoom-out feature 39.

Still referring to FIG. 12 and referring back to FIGS. 4 and 9, in the system S, the end effector status window 53 comprises at least one end effector icon 53a, each of the at least one end effector icon 53a corresponding to at least one end effector control feature of an end effector handle (FIG. 1), the at least one end effector control feature comprising at least one of a zoom control feature, e.g., a zoom adjustment switch 13a, and focus control feature, e.g., the focus adjustment switch 13b (FIG. 1), wherein the at least one end effector icon 53a comprises a color, wherein the color comprises one of a gray color and a blue color, wherein the gray color indicates that a corresponding function is not being performed by the end effector 10, and wherein the blue color indicates that a corresponding function is being performed by the end effector 10.

Figure 13:
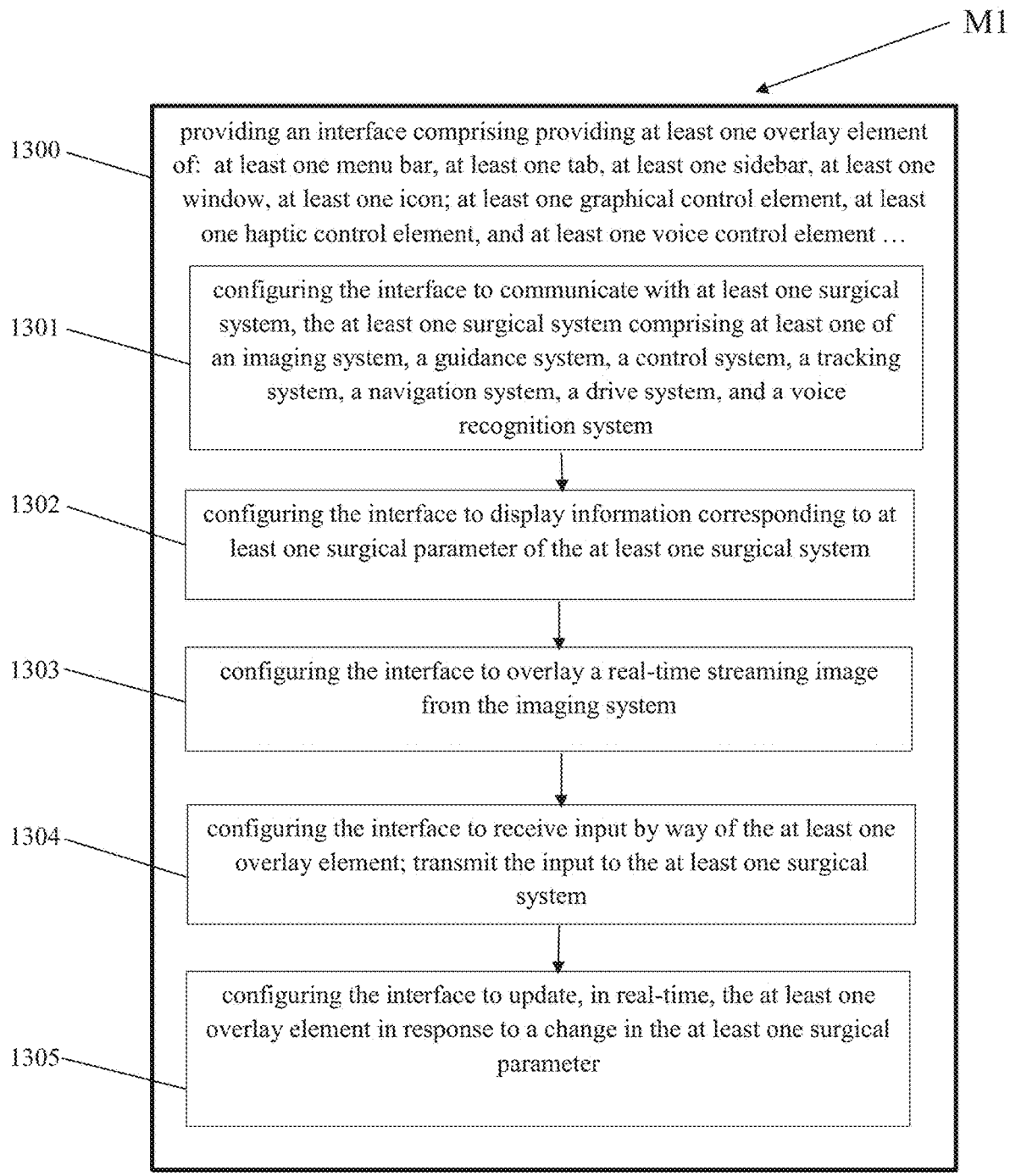
FIG. 13 is a flow diagram illustrating a method of providing a surgical user interface system, in accordance with an embodiment of the present disclosure.

Referring to FIG. 13, this flow diagram illustrating a method M1 of providing a surgical user interface system S, in accordance with an embodiment of the present disclosure. The method M1 comprises: providing an interface, e.g., an interface corresponding to screens 40, 900, 1200, and the like, comprising providing at least one overlay element of: at least one menu bar, at least one tab, at least one sidebar, at least one window, at least one icon; at least one graphical control element, at least one haptic control element, and at least one voice control element, as indicated by block 1300, providing the interface comprising configuring the interface to: communicate with at least one surgical system, the at least one surgical system comprising at least one of an imaging system, a guidance system, a control system, a tracking system, a navigation system, a drive system, and a voice recognition system, as indicated by block 1301; display information corresponding to at least one surgical parameter of the at least one surgical system, as indicated by block 1302; overlay a real-time streaming image 200 from the imaging system, as indicated by block 1303; receive input by way of the at least one overlay element; transmit the input to the at least one surgical system, as indicated by block 1304; and update, in real-time, the at least one overlay element in response to a change in the at least one surgical parameter, as indicated by block 1305.

Still referring to FIG. 13, in the method M1, providing the at least one overlay element of the at least one sidebar comprises at least one of: providing a tool tracking sidebar, e.g., the tool sidebar 41, configured to communicate with the tracking system, providing the tool tracking sidebar comprising providing at least one tool tracking icon, e.g., the tool icons 41a through 41e, providing the at least one tool tracking icon comprising providing each tool icon of the at least one tool icon corresponding to at least one surgical tool; and providing a reference tracking sidebar, e.g., the reference sidebar 42, configured to communicate with the tracking system, providing the reference tracking sidebar comprising providing at least one reference tracking icon, e.g., the reference icons 42a through 42c, providing the at least one reference tracking icon comprising providing each reference icon of the at least one reference tracking icon corresponding to at least one reference object.

Still referring to FIG. 13, in the method M1, providing the at least one tool tracking icon, e.g., the tool icons 41a through 41e, comprises corresponding the at least one tool tracking icon to at least one surgical tool of a tracked pointer tool, a tracked calibration tool, and a tracked suction tool, a tracked resection tool, and providing at least one reference tracking icon comprises corresponding the at least one reference object to at least one of a patient reference object, and end effector, and a calibration apparatus. Providing the at least one tool tracking icon comprises providing each tool tracking icon with a color, providing each tool tracking icon with the color comprising configuring the color as real-time updateable in response to at least one of tracking and navigating registration of each corresponding at least one surgical tool. Providing each tool tracking icon with the color comprises one of providing a red color, providing a yellow color, and providing a green color, wherein providing the red color indicates that the corresponding at least one surgical tool is not registered, wherein the providing yellow color indicates that the corresponding at least one surgical tool is within a predetermined threshold of being registered, and wherein the providing green color indicates that the corresponding at least one surgical tool is registered.

Still referring to FIG. 13, in the method M1, providing the at least one menu bar comprises at least one of: providing a notification icon 43, providing the notification icon comprising configuring the notification icon 543 to render if at least one notification is received from the drive or guidance system; and providing a status and task menu bar 44, providing the status and task bar comprising at least one of providing a video recording icon 44a, providing a mark log icon 44b, providing a video overlay icon 44c, providing a tracking camera icon 44d, providing a settings icon 44e, providing a help icon 44f, and providing a caster brake icon (not shown).

Still referring to FIG. 13, in the method M1, providing the notification icon 43 comprises providing a representation of an exclamation mark disposed within a triangle, providing the notification icon comprises providing a color, providing the color comprising configuring the color as real-time updateable in response to a corresponding change in the drive or guidance system, providing the color comprises one of providing a red color and providing a yellow color, providing the red color indicates an error arising from a change in the at least one surgical system which will result in patient injury, and providing the yellow color indicates a warning arising from a change in the at least one surgical system which may result in patient injury.

Still referring to FIG. 13, in the method M1, providing the video recording icon comprises configuring the video recording icon 44a to toggle for respectively commencing and terminating video recording. Providing the mark log icon 44b comprises configuring the mark log icon 44b to toggle for adding a flag to a log of the guidance system. Providing the video overlay icon 44c comprises configuring the video overlay icon 44c to toggle for one of displaying and hiding the at least one overlay element. Providing the tracking camera icon 44d comprises configuring the tracking camera icon 44d to toggle for indicating a status of the drive or guidance system in relation to the tracking system. Providing the settings icon 44e comprises configuring the settings icon 44e to toggle for accessing at least one of at least one setting and at least one option of the drive or guidance system. Providing the help icon 44f comprises configuring the help icon 44f to toggle for accessing help information. Providing the caster brake icon (not shown) comprises configuring the caster brake icon to toggle for indicating a status of a caster brake.

Still referring to FIG. 13, in the method M1, providing the at least one overlay element of the at least one window comprises at least one of providing a pose setup window 45, providing an optical device alignment options window 46, providing a position memory window 47, providing a position history window 48, providing a camera and light controls window 49, providing a notification dialog box 51, providing a foot pedal status window 52, and providing an end effector status window 53. Providing the pose setup window 45 comprises providing a set pose button 45a and providing a reset button 45b. Providing the set pose button 45a comprises configuring the set pose button 45a to set a position of the at least one surgical tool in relation to an end effector 10 as a current position, whereby the position defines a pose set. Providing the reset button 45b comprises configuring the reset button 45b to set the position of the at least one surgical tool in relation to the end effector 10 as a default position.

Still referring to FIG. 13, in the method M1, providing the optical device alignment options window 46 comprises at least one of providing a point button 46a, providing an axis adjustment button 46b, and providing an axis rotation button 46c. Providing the point button 46a comprises configuring the point button 46a to initiate an instruction to the drive guidance system for moving an arm with the end effector 10 to position a camera of the tracking system, whereby the camera is oriented toward a desired portion of the at least one surgical tool. Providing the axis adjustment button 46b comprises configuring the axis adjustment button 46b to initiate an instruction to the drive guidance system for moving the arm with the end effector 10 to position the camera of the tracking system, whereby the camera is oriented toward a desired portion of the at least one surgical tool, and whereby the camera is aligned with the at least one surgical tool at an angle relative to a major axis of the at least one surgical tool, the angle specified by the pose set. Providing the axis rotation button 46c comprises configuring the axis rotation button 46c to initiate an instruction to the drive or guidance system for moving the arm with the end effector 10 to position the camera of the tracking system, whereby the camera is oriented toward a desired portion of the at least one surgical tool, whereby the camera is aligned with the at least one surgical tool at an angle relative to a major axis of the at least one surgical tool, the angle specified by the pose set, and whereby the camera is aligned with the at least one surgical tool at a rotation, the rotation specified by the pose set.

Still referring to FIG. 13, in the method M1, providing the position memory window 47 comprises providing at least one add or memory position button configured to toggle for recording a new memory position. For example, the position memory window 47 comprises a plurality of memory position buttons 47a, 47b, 47c, 47d, 47e, each memory position button or icon having a "plus" sign representation for saving position information and configured to toggle for recording a new memory position. Providing the at least one add or memory position button comprises providing at least one numbered memory position button, e.g., buttons 47a, 47b, 47c. Providing the at least one numbered memory position button comprises configuring the at least one numbered memory position button to receive input corresponding to at least one actuation of a foot pedal 30 of the drive or guidance system. Providing the at least one numbered memory position button comprises configuring the at least one numbered memory position button to initiate at least one of resetting a memory position and deleting a memory position.

Still referring to FIG. 13, in the method M1, providing the position history window 48 comprises providing an undo button 48a and providing a redo button 48b, wherein providing the undo button 48a comprises configuring the undo button 48b to initiate an instruction to the drive or guidance system for moving the arm with the end effector 10 into a previous position in response to an actuation of a foot pedal 30, and wherein providing the redo button 48b comprises configuring the redo button 48b to initiate an instruction to the drive or guidance system for moving the arm with the end effector 10 into an original position in response to an actuation of a foot pedal 30.

Still referring to FIG. 13, in the method M1, providing the camera and light controls window 49 comprises at least one of: providing a camera preset adjustment feature comprising at least one of a field selection feature 49a and a white balance control feature 49b, providing a magnification adjustment feature 49c, providing a focal distance adjustment feature 49d, and providing an incremental light adjustment feature 49e. Providing the notification dialog box 51 comprises providing at least one notification region 51a, 51b for respectively displaying at least one of a warning 51a' and a notification relating to a surgical task being performed 51b'. Providing the foot pedal status window 52 comprises providing at least one foot pedal function icon 52a corresponding to at least one function of a multi-function foot pedal 30 of a drive or guidance system. Providing the at least one foot pedal function icon 52a comprises providing a color, wherein providing the color comprises one of providing a gray color and providing a blue color, wherein providing the gray color indicates that a corresponding function is not being performed by the multi-function foot pedal 30, and wherein providing the blue color indicates that a corresponding function is being performed by the multi-function foot pedal 30.

Still referring to FIG. 13, in the method M1, providing the end effector status window 53 comprises providing at least one end effector icon 53a, providing the end effector status window 53 comprises providing each of the at least one end effector icon 53a corresponding to at least one end effector control feature of an end effector handle 12, the at least one end effector control feature comprising at least one of a zoom control feature, e.g., a zoom adjustment switch 13a, and focus control feature, e.g., the focus adjustment switch 13b (FIG. 1), wherein providing the at least one end effector icon 53a comprises providing a color, wherein providing the color comprises one of providing a gray color and providing a blue color, wherein providing the gray color indicates that a corresponding function is not being performed by the end effector 10, and wherein providing the blue color indicates that a corresponding function is being performed by the end effector 10.

Figure 14:
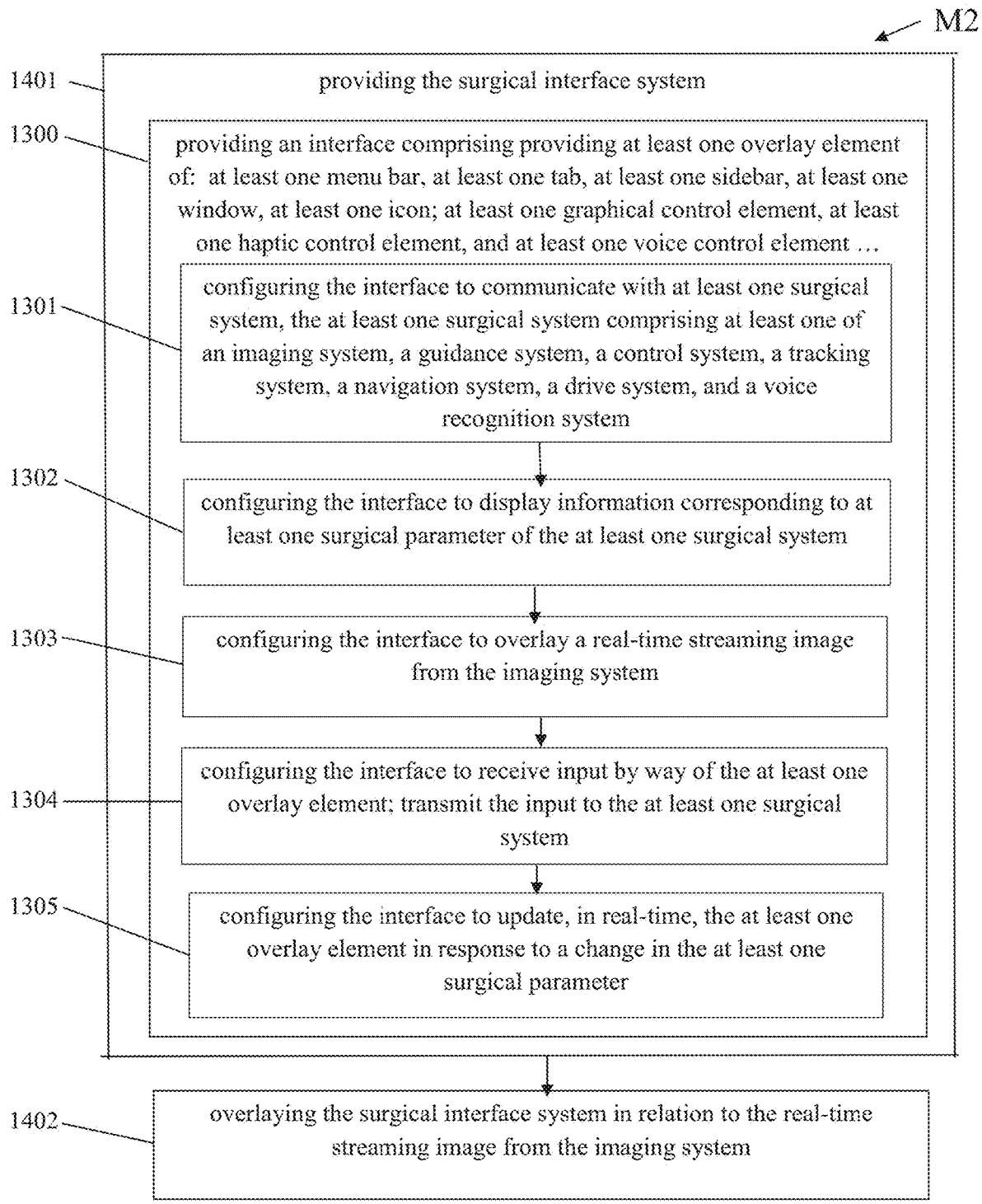
FIG. 14 is a flow diagram illustrating a method of interfacing at least one surgical system by way of a surgical user interface system, in accordance with an embodiment of the present disclosure.

Referring to FIG. 14, this flow diagram illustrating a method M2 of interfacing at least one surgical system, such as a tracking system, an imaging system, a guidance or drive system, and the like, by way of a surgical user interface system S, in accordance with an embodiment of the present disclosure. The method M2 comprises: providing the surgical interface system, as indicated by block 1401, providing the surgical interface system comprising providing an interface, providing the interface, e.g., an interface corresponding to screens 40, 900, 1200, and the like, comprising providing at least one overlay element of: at least one menu bar, at least one tab, at least one sidebar, at least one window, at least one icon; at least one graphical control element, at least one haptic control element, and at least one voice control element, as indicated by block 1300, providing the interface comprising configuring the interface to: communicate with at least one surgical system, the at least one surgical system comprising at least one of an imaging system, a guidance system, a control system, a tracking system, a navigation system, a drive system, and a voice recognition system, as indicated by block 1301; display information corresponding to at least one surgical parameter of the at least one surgical system, as indicated by block 1302; overlay a real-time streaming image from the imaging system, as indicated by block 1303; receive input by way of the at least one overlay element; transmit the input to the at least one surgical system, as indicated by block 1304; and update, in real-time, the at least one overlay element in response to a change in the at least one surgical parameter, as indicated by block 1305; and overlaying the surgical interface system in relation to the a real-time streaming image from the imaging system, as indicated by block 1402.

At least some aspects disclosed are embodied, at least in part, in software. That is, some disclosed techniques and methods are carried out in a computer system or other data processing system in response to its processor, such as a microprocessor, executing sequences of instructions contained in a memory, such as ROM, volatile RAM, non-volatile memory, cache or a remote storage device.

A computer readable storage medium is used to store software and data which when executed by a data processing system causes the system to perform various methods or techniques of the present disclosure. The executable software and data is stored in various places including for example ROM, volatile RAM, non-volatile memory and/or cache. Portions of this software and/or data are stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium is the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium is provided in various forms such as, but not limited to, one or more diskettes, compact disks, tapes, chips, universal server bus (USB) keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein are implemented by software, or a combination of software and hardware. Elements of the system that are implemented via software are written in a high-level programming language such as object-oriented programming or a scripting language. Accordingly, the program code is written in C, C++, J++, or any other suitable programming language and may comprise functions, modules or classes, as is known to those skilled in computer programming. At least some of the elements of the system that are implemented via software are written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner for performing at least one of the methods described herein.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, any particular order to steps or stages of methods or processes described in this disclosure is not intended or implied. In many cases the order of process steps is varied without changing the purpose, effect, or import of the methods described.

Information as herein shown and described in detail is fully capable of attaining the above-described embodiments of the present disclosure and the presently preferred embodiment, if any, of the present disclosure, and is, thus, representative of the subject matter which is broadly contemplated by the present disclosure. The scope of the present disclosure fully encompasses other embodiments and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a device, an apparatus, a system, or a method to address each, and every, problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail is made, without departing from the spirit and scope of the present disclosure, as set forth in the appended claims, as is apparent, or may become apparent, to those of ordinary skill in the art, are also encompassed by the present disclosure.

INDUSTRIAL APPLICABILITY

Generally, the present disclosure industrially applies to user interface systems and methods. More particularly, the present disclosure industrially applies to user interface systems and methods for surgical systems. Even more particularly, the present disclosure industrially applies to user interface systems and methods for overlaying surgical video output from a surgical system.

What is claimed:

1. A surgical user interface system, comprising:
an interface comprising at least one overlay element of: a menu bar, at least one tab, at least one sidebar, at least one window, at least one icon; at least one graphical control element, at least one haptic control element, at least one voice control element, or any combination thereof, the interface configured to:
communicate with at least one surgical system, the at least one surgical system comprising at least one of: an imaging system, a guidance system, a control system, a tracking system, a navigation system, a drive system, a voice recognition system, or any combination thereof;
display information corresponding to at least one surgical parameter of the at least one surgical system;
overlay a real-time streaming image from the imaging system;
receive input by way of the at least one overlay element;
transmit the input to the at least one surgical system; and
update, in real-time, the at least one overlay element in response to a change in the at least one surgical parameter,
the menu bar comprising: a notification icon, the notification icon configured to render if a one notification is received from the guidance system; and a status and task menu bar, the status and task bar comprising at least one of: a video recording icon, a mark log icon, a video overlay icon, a tracking camera icon, a settings icon, a help icon, a caster brake icon, or any combination thereof,
the video recording icon configured to toggle for respectively commencing and terminating video recording,
the mark log icon configured to toggle for adding a flag to a log of the guidance system,
the video overlay icon configured to toggle for respectively displaying or hiding the at least one overlay element,
the tracking camera icon configured to toggle for indicating a status of the guidance system in relation to the tracking system,
the settings icon configured to toggle for accessing at least one of: a setting, an option of the guidance system, or a combination thereof,
the help icon configured to toggle for accessing help information, and
the caster brake icon configured to toggle for indicating a status of a caster brake.

2. The system of claim 1, wherein the at least one sidebar comprises at least one of:
a tool tracking sidebar configured to communicate with the tracking system, the tool tracking sidebar comprising at least one tool tracking icon, each tool icon of the at least one tool icon corresponding to at least one surgical tool; and
a reference tracking sidebar configured to communicate with the tracking system, the reference tracking sidebar comprising at least one reference tracking icon, each reference icon of the at least one reference tracking icon corresponding to at least one reference object.

3. The system of claim 2,
wherein the at least one surgical tool comprises at least one of a tracked pointer tool, a tracked calibration tool, and a tracked suction tool, a tracked resection tool, and
wherein the at least one reference object comprises at least one of a patient reference object, and end effector, and a calibration apparatus.

4. The system of claim 2, wherein each tool tracking icon comprises a color, the color being real-time updateable in response to at least one of tracking and navigating registration of each corresponding at least one surgical tool.

5. The system of claim 4,
wherein the color comprises one of a red color, a yellow color, and a green color,
wherein the red color indicates that the corresponding at least one surgical tool is not registered,
wherein the yellow color indicates that the corresponding at least one surgical tool is within a predetermined threshold of being registered, and
wherein the green color indicates that the corresponding at least one surgical tool is registered.

6. The system of claim 1,
wherein the notification icon comprises a representation of an exclamation mark disposed within a triangle,
wherein the notification icon comprises a color, the color being real-time updateable in response to a change in the guidance system,
wherein the color comprises one of a red color and a yellow color,
wherein the red color comprises one of a red color and a yellow color,
wherein the red color indicates an error arising corresponding to a change in the at least one surgical system which will result in patient injury, and
wherein the yellow color indicated a warning corresponding to a change in the at least one surgical system which may result in patient injury.

7. The system of claim 1, wherein the at least one window comprises at least one of a pose setup window, an optical device alignment window, a position memory window, a position history window, a camera and light controls window, a notification icon dialog box, a foot pedal status window, and an end effector status window.

8. The system of claim 7, wherein the pose setup window comprises a set pose button and a reset button, wherein the set pose button is configured to set a position of the at least one surgical tool in relation to an end effector as a current position, whereby the position defines a pose set, and wherein the reset button is configured to set the position of the at least one surgical tool in relation to the end effector as a default position.

9. The system of claim 7,
wherein the optical device alignment window comprises at least one of a point button, an axis button, and an axis rotation button,
wherein the point button is configured to initiate an instruction to the guidance system for moving an arm to position a camera of the tracking system, whereby the camera is oriented toward a desired portion of the at least one surgical tool,
wherein the axis button is configured to initiate an instruction to the guidance system for moving the arm to position the camera of the tracking system, whereby the camera is oriented toward a desired portion of the at least one surgical tool, and whereby the camera is aligned with the at least one surgical tool at an angle relative to a major axis of the at least one surgical tool, the angle specified by the pose set, and wherein the axis rotation button is configured to initiate an instruction to the guidance system for moving the arm to position the camera of the tracking system, whereby the camera is oriented toward a desired portion of the at least one surgical tool, whereby the camera is aligned with the at least one surgical tool at an angle relative to a major axis of the at least one surgical tool, the angle specified by the pose set, and whereby the camera is aligned with the at least one surgical tool at a rotation, the rotation specified by the pose set.

10. The system of claim 7, wherein the position memory window comprises at least one add button configured to toggle for recording a new memory position, wherein the at least one add button becomes at least one numbered memory position button, wherein the at least one numbered memory position button is configured to receive input corresponding to at least one actuation of a foot pedal of the guidance system, wherein the at least one numbered memory position button is configured to initiate at least one of resetting a memory position and deleting a memory position.

11. The system of claim 7, wherein the position history window comprises an undo button and a redo button, wherein the undo button is configured to initiate an instruction to the guidance system for moving the arm into a previous position in response to an actuation of a foot pedal, and wherein the redo button is configured to initiate an instruction to the guidance system for moving the arm into an original position in response to an actuation of a foot pedal.

12. The system of claim 7, wherein the camera and light controls window comprises at least one of: a camera preset adjustment feature comprising at least one of a field selection feature and a white balance control feature, a magnification adjustment feature, a focal distance adjustment feature, and an incremental light adjustment feature.

13. The system of claim 7, wherein the notification dialog box comprises at least one notification region for displaying at least one of a warning and a notification relating to a surgical task being performed.

14. The system of claim 7, wherein the foot pedal status window comprises at least one foot pedal function icon corresponding to at least one function of a multi-function foot pedal of a guidance system, wherein the at least one foot pedal function icon comprises a color, wherein the color comprises one of a gray color and a blue color, wherein the gray color indicates that a corresponding function is not being performed by the multi-function foot pedal, and wherein the blue color indicates that a corresponding function is being performed by the multi-function foot pedal.

15. The system of claim 7, wherein the end effector status window comprises at least one end effector icon, each of the at least one end effector icon corresponding to at least one end effector control feature of an end effector handle, the at least one end effector control feature comprising at least one of a zoom control feature and focus control feature, wherein the at least one end effector icon comprises a color, wherein the color comprises one of a gray color and a blue color, wherein the gray color indicates that a corresponding function is not being performed by the end effector, and wherein the blue color indicates that a corresponding function is being performed by the end effector.

16. A method of providing a surgical user interface system, comprising:
providing an interface,
providing the interface comprising providing at least one overlay element of: a menu bar, at least one tab, at least one sidebar, at least one window, at least one icon; at least one graphical control element, at least one haptic control element, at least one voice control element, or any combination thereof; and
configuring the interface to:
communicate with at least one surgical system, the at least one surgical system comprising at least one of: an imaging system, a guidance system, a control system, a tracking system, a navigation system, a drive system, a voice recognition system, and any combination thereof;
display information corresponding to at least one surgical parameter of the at least one surgical system;
overlay a real-time streaming image from the imaging system;
receive input by way of the at least one overlay element;
transmit the input to the at least one surgical system; and
update, in real-time, the at least one overlay element in response to a change in the at least one surgical parameter,
providing the menu bar comprising: providing a notification icon, providing the notification icon comprising configuring the notification icon to render if at least one notification is received from the guidance system; and providing a status and task menu bar, providing the status and task bar comprising at least one of: providing a video recording icon, providing a mark log icon, providing a video overlay icon, providing a tracking camera icon, providing a settings icon, providing a help icon, providing a caster brake icon, or any combination thereof,
providing the video recording icon comprising configuring the video recording icon to toggle for respectively commencing and terminating video recording,
providing the mark log icon comprising configuring the mark log icon to toggle for adding a flag to a log of the guidance system,
providing the video overlay icon comprising configuring the video overlay icon to toggle for one of displaying and hiding the at least one overlay element,
providing the tracking camera icon comprising configuring the tracking camera icon to toggle for indicating a status of the guidance system in relation to the tracking system,
providing the settings icon comprising configuring the settings icon to toggle for accessing at least one of: a setting, an option of the guidance system, and a combination thereof,
providing the help icon comprising configuring the help icon to toggle for accessing help information, and
providing the caster brake icon comprising configuring the caster brake icon to toggle for indicating a status of a caster brake.

17. The method of claim 16, wherein providing the at least one overlay element of the at least one sidebar comprises at least one of:
providing a tool tracking sidebar configured to communicate with the tracking system, providing the tool tracking sidebar comprising providing at least one tool tracking icon, providing the at least one tool tracking icon comprising providing each tool icon of the at least one tool icon corresponding to at least one surgical tool; and providing a reference tracking sidebar configured to communicate with the tracking system, providing the reference tracking sidebar comprising providing at least one reference tracking icon, providing the at least one reference tracking icon comprising providing each reference icon of the at least one reference tracking icon corresponding to at least one reference object.

18. The method of claim 17,
wherein providing the at least one tool tracking icon comprises corresponding the at least one tool tracking icon to at least one surgical tool of a tracked pointer tool, a tracked calibration tool, and a tracked suction tool, a tracked resection tool, and
wherein providing at least one reference tracking icon comprises corresponding the at least one reference object to at least one of a patient reference object, and end effector, and a calibration apparatus.

19. The method of claim 17, wherein providing the at least one tool tracking icon comprises providing each tool tracking icon with a color, providing each tool tracking icon with the color comprising configuring the color as real-time updateable in response to at least one of tracking and navigating registration of each corresponding at least one surgical tool.

20. The method of claim 19,
wherein providing each tool tracking icon with the color comprises one of providing a red color, providing a yellow color, and providing a green color,
wherein providing the red color indicates that the corresponding at least one surgical tool is not registered,
wherein the providing yellow color indicates that the corresponding at least one surgical tool is within a predetermined threshold of being registered, and
wherein the providing green color indicates that the corresponding at least one surgical tool is registered.

21. The method of claim 16,
wherein providing the notification icon comprises providing a representation of an exclamation mark disposed within a triangle,
wherein providing the notification icon comprises providing a color, providing the color comprising configuring the color as real-time updateable in response to a corresponding change in the guidance system,
wherein providing the color comprises one of providing a red color and providing a yellow color,
wherein providing the red color indicates an error arising from a change in the at least one surgical system which will result in patient injury, and
wherein providing the yellow color indicates a warning arising from a change in the at least one surgical system which may result in patient injury.

22. The method of claim 16, wherein providing the at least one overlay element of the at least one window comprises at least one of providing a pose setup window, providing an optical device alignment window, providing a position memory window, providing a position history window, providing a camera and light controls window, providing a notification dialog box, providing a foot pedal status window, and providing an end effector status window.

23. The method of claim 22,
wherein providing the pose setup window comprises providing a set pose button and providing a reset button,
wherein providing the set pose button comprises configuring the set pose button to set a position of the at least one surgical tool in relation to an end effector as a current position, whereby the position defines a pose set, and
wherein providing the reset button comprises configuring the reset button to set the position of the at least one surgical tool in relation to the end effector as a default position.

24. The method of claim 22,
wherein providing the optical device alignment window comprises at least one of providing a point button, providing an axis button, and providing an axis rotation button,
wherein providing the point button comprises configuring the point button to initiate an instruction to the guidance system for moving an arm to position a camera of the tracking system, whereby the camera is oriented toward a desired portion of the at least one surgical tool,
wherein providing the axis button comprises configuring the axis button to initiate an instruction to the guidance system for moving the arm to position the camera of the tracking system, whereby the camera is oriented toward a desired portion of the at least one surgical tool, and whereby the camera is aligned with the at least one surgical tool at an angle relative to a major axis of the at least one surgical tool, the angle specified by the pose set, and
wherein providing the axis rotation button comprises configuring the axis rotation to initiate an instruction to the guidance system for moving the arm to position the camera of the tracking system, whereby the camera is oriented toward a desired portion of the at least one surgical tool, whereby the camera is aligned with the at least one surgical tool at an angle relative to a major axis of the at least one surgical tool, the angle specified by the pose set, and whereby the camera is aligned with the at least one surgical tool at a rotation, the rotation specified by the pose set.

25. The method of claim 22,
wherein providing the position memory window comprises providing at least one add button configured to toggle for recording a new memory position,
wherein providing the at least one add button comprises providing at least one numbered memory position button,
wherein providing the at least one numbered memory position button comprises configuring the at least one numbered memory position button to receive input corresponding to at least one actuation of a foot pedal of the guidance system,
wherein providing the at least one numbered memory position button comprises configuring the at least one numbered memory position button to initiate at least one of resetting a memory position and deleting a memory position,
wherein providing the position history window comprises providing an undo button and providing a redo button,
wherein providing the undo button comprises configuring the undo button to initiate an instruction to the guidance system for moving the arm into a previous position in response to an actuation of a foot pedal, and
wherein providing the redo button comprises configuring the redo button to initiate an instruction to the guidance system for moving the arm into an original position in response to an actuation of a foot pedal.

26. The method of claim 22,
wherein providing the camera and light controls window comprises at least one of: providing a camera preset adjustment feature comprising at least one of a field selection feature and a white balance control feature, providing a magnification adjustment feature, providing a focal distance adjustment feature, and providing an incremental light adjustment feature,
wherein providing the notification dialog box comprises providing at least one notification region for displaying at least one of a warning and a notification relating to a surgical task being performed,
wherein providing the foot pedal status window comprises providing at least one foot pedal function icon corresponding to at least one function of a multi-function foot pedal of a guidance system,
wherein providing the at least one foot pedal function icon comprises providing a color,
wherein providing the color comprises one of providing a gray color and providing a blue color,
wherein providing the gray color indicates that a corresponding function is not being performed by the multi-function foot pedal, and
wherein providing the blue color indicates that a corresponding function is being performed by the multi-function foot pedal,
wherein providing the end effector status window comprises providing at least one end effector icon, providing the end effector status window comprises providing each of the at least one end effector icon corresponding to at least one end effector control feature of an end effector handle, the at least one end effector control feature comprising at least one of a zoom control feature and focus control feature,
wherein providing the at least one end effector icon comprises providing a color,
wherein providing the color comprises one of providing a gray color and providing a blue color,
wherein providing the gray color indicates that a corresponding function is not being performed by the end effector, and
wherein providing the blue color indicates that a corresponding function is being performed by the end effector.

27. A method of interfacing at least one surgical system by way of a surgical user interface system, comprising:
providing the surgical interface system, providing the surgical interface system comprising providing an interface comprising at least one overlay element of: a menu bar, at least one tab, at least one sidebar, at least one window, at least one icon; at least one graphical control element, at least one haptic control element, at least one voice control element, or any combination thereof; and
configuring the interface to:
communicate with at least one surgical system, the at least one surgical system comprising at least one of: an imaging system, a guidance system, a control system, a tracking system, a navigation system, a drive system, a voice recognition system, or any combination thereof;
display information corresponding to at least one surgical parameter of the at least one surgical system;
overlay a real-time streaming image from the imaging system;
receive input by way of the at least one overlay element;
transmit the input to the at least one surgical system; and
update, in real-time, the at least one overlay element in response to a change in the at least one surgical parameter,
providing the menu bar comprising: providing a notification icon, providing the notification icon comprising configuring the notification icon to render if at least one notification is received from the guidance system; and providing a status and task menu bar, providing the status and task bar comprising at least one of: providing a video recording icon, providing a mark log icon, providing a video overlay icon, providing a tracking camera icon, providing a settings icon, providing a help icon, providing a caster brake icon, or any combination thereof,
providing the video recording icon comprising configuring the video recording icon to toggle for respectively commencing and terminating video recording,
providing the mark log icon comprising configuring the mark log icon to toggle for adding a flag to a log of the guidance system,
providing the video overlay icon comprising configuring the video overlay icon to toggle for one of displaying and hiding the at least one overlay element,
providing the tracking camera icon comprising configuring the tracking camera icon to toggle for indicating a status of the guidance system in relation to the tracking system,
providing the settings icon comprising configuring the settings icon to toggle for accessing at least one of: a setting, an option of the guidance system, and a combination thereof,
providing the help icon comprising configuring the help icon to toggle for accessing help information, and
providing the caster brake icon comprising configuring the caster brake icon to toggle for indicating a status of a caster brake; and
overlaying the surgical interface system in relation to the a real-time streaming image from the imaging system.

* * * * *